US007258692B2

(12) United States Patent
Thelen et al.

(10) Patent No.: US 7,258,692 B2
(45) Date of Patent: Aug. 21, 2007

(54) METHOD AND APPARATUS FOR REDUCING FEMORAL FRACTURES

(75) Inventors: Sarah L. Thelen, North Manchester, IN (US); Antony J. Lozier, Warsaw, IN (US); Steven E. Dietzel, Peru, IN (US); Billy N. Sisk, Claypool, IN (US); Rick Miller, South Whitley, IN (US); Gregory C. Stalcup, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 130 days.

(21) Appl. No.: 10/155,683

(22) Filed: May 23, 2002

(65) Prior Publication Data

US 2003/0220641 A1    Nov. 27, 2003

Related U.S. Application Data

(63) Continuation-in-part of application No. 09/520,351, filed on Mar. 7, 2000, now Pat. No. 6,447,514.

(51) Int. Cl.
*A61B 17/56* (2006.01)
*A61F 2/30* (2006.01)

(52) U.S. Cl. .......................................... 606/62

(58) Field of Classification Search ................. 606/60, 606/62, 63, 64
See application file for complete search history.

(56) References Cited

U.S. PATENT DOCUMENTS 3,128,768 A    4/1964    Mikelis (Continued)

FOREIGN PATENT DOCUMENTS

EP    0 496 636    7/1992

(Continued)

OTHER PUBLICATIONS pp. 61-62, Chapter 1, Campbell's Operative Orthopedics, Edited by S. Terry Canale, vol. 1, Tenth Edition.*

(Continued)

*Primary Examiner*—Anu Ramana
(74) *Attorney, Agent, or Firm*—Baker & Daniels LLP

(57) ABSTRACT

An improved method and apparatus for reducing a hip fracture utilizing a minimally invasive procedure which does not require incision of the quadriceps. A femoral implant in accordance with the present invention achieves intramedullary fixation as well as fixation into the femoral head to allow for the compression needed for a femoral fracture to heal. To position the femoral implant of the present invention, an incision is made along the greater trochanter. Because the greater trochanter is not circumferentially covered with muscles, the incision can be made and the wound developed through the skin and fascia to expose the greater trochanter, without incising muscle, including, e.g., the quadriceps. After exposing the greater trochanter, novel instruments of the present invention are utilized to prepare a cavity in the femur extending from the greater trochanter into the femoral head and further extending from the greater trochanter into the intramedullary canal of the femur. After preparation of the femoral cavity, a femoral implant in accordance with the present invention is inserted into the aforementioned cavity in the femur. The femoral implant is thereafter secured in the femur, with portions of the implant extending into and being secured within the femoral head and portions of the implant extending into and being secured within the femoral shaft.

29 Claims, 31 Drawing Sheets

U.S. PATENT DOCUMENTS

| | | | |
|---|---|---|---|
| 3,991,600 A | 11/1976 | Del Fabro | |
| 4,285,618 A | 8/1981 | Shanley, Jr. | |
| 4,313,434 A | 2/1982 | Segal | 128/92 BC |
| 4,438,762 A | 3/1984 | Kyle | |
| 4,653,489 A | 3/1987 | Tronzo | 128/92 YV |
| 4,662,887 A | 5/1987 | Turner et al. | 623/16 |
| 4,714,478 A * | 12/1987 | Fischer | 623/22.4 |
| 4,776,330 A * | 10/1988 | Chapman et al. | 606/64 |
| 4,777,942 A | 10/1988 | Frey | |
| 4,969,888 A | 11/1990 | Scholten et al. | 606/94 |
| 5,061,287 A * | 10/1991 | Feiler | 623/23.48 |
| 5,102,413 A | 4/1992 | Poddar | |
| 5,108,404 A | 4/1992 | Scholten et al. | 606/94 |
| 5,303,718 A | 4/1994 | Krajicek | 128/897 |
| 5,312,408 A | 5/1994 | Brown | |
| 5,342,363 A | 8/1994 | Richelsoph | |
| 5,376,123 A | 12/1994 | Klaue et al. | |
| 5,403,320 A | 4/1995 | Luman | |
| 5,423,850 A | 6/1995 | Berger | 606/192 |
| 5,429,641 A * | 7/1995 | Gotfried | 606/67 |
| 5,462,547 A | 10/1995 | Weigum | |
| 5,480,400 A | 1/1996 | Berger | 606/60 |
| 5,514,137 A | 5/1996 | Coutts | 606/62 |
| 5,527,316 A | 6/1996 | Stone et al. | |
| 5,540,694 A | 7/1996 | DeCarlo | |
| 5,549,679 A | 8/1996 | Kuslich | 623/17 |
| 5,558,134 A | 9/1996 | Miyazaki | |
| 5,571,189 A | 11/1996 | Kuslich | 623/17 |
| 5,591,168 A | 1/1997 | Judet et al. | |
| 5,624,447 A | 4/1997 | Myers | |
| 5,649,930 A | 7/1997 | Kertzner | |
| 5,658,310 A | 8/1997 | Berger | 606/192 |
| 5,681,289 A | 10/1997 | Wilcox et al. | 604/175 |
| 5,690,671 A | 11/1997 | McGurk | |
| 5,827,289 A | 10/1998 | Reiley et al. | 606/86 |
| 5,908,423 A | 6/1999 | Kashuba et al. | |
| 5,951,160 A | 9/1999 | Ronk | 366/130 |
| 5,976,139 A | 11/1999 | Bramlet | |
| 5,997,582 A | 12/1999 | Weiss | 623/23 |
| 6,053,922 A | 4/2000 | Krause et al. | |
| 6,066,154 A | 5/2000 | Reiley et al. | |
| 6,096,042 A | 8/2000 | Herbert | |
| 6,110,211 A | 8/2000 | Weiss | |
| 6,156,069 A | 12/2000 | Amstutz | |
| 6,228,091 B1 | 5/2001 | Axelson, Jr. et al. | |
| 6,235,043 B1 | 5/2001 | Reiley et al. | 606/192 |
| 6,241,734 B1 | 6/2001 | Scribner et al. | 606/93 |
| 6,248,110 B1 * | 6/2001 | Reiley et al. | 606/93 |
| 6,261,289 B1 * | 7/2001 | Levy | 606/63 |
| 6,358,251 B1 | 3/2002 | Mirza | |
| 6,425,923 B1 | 7/2002 | Stalcup et al. | 623/23.58 |
| 6,447,514 B1 | 9/2002 | Stalcup et al. | 606/63 |
| 6,562,042 B2 * | 5/2003 | Nelson | 606/62 |
| 6,613,054 B2 | 9/2003 | Scribner et al. | 606/93 |
| 6,616,697 B2 * | 9/2003 | Sotereanos | 623/23.26 |
| 6,740,090 B1 | 5/2004 | Cragg et al. | |
| 6,755,862 B2 | 6/2004 | Keynan | 623/16.11 |
| 6,755,865 B2 | 6/2004 | Tarabishy | |
| 2001/0034526 A1 | 10/2001 | Kuslich | |
| 2002/0010472 A1 | 1/2002 | Kuslich et al. | |
| 2002/0022847 A1 | 2/2002 | Ray et al. | |
| 2002/0193799 A1 | 12/2002 | Veldman | |

FOREIGN PATENT DOCUMENTS

| | | |
|---|---|---|
| EP | 0 617 927 | 10/1994 |
| EP | 1 132 051 | 9/2001 |
| EP | 1 312 051 | 9/2001 |
| EP | 1132051 A2 | 9/2001 |
| EP | 1132053 A1 | 9/2001 |
| EP | 03253269.9 | 9/2001 |
| EP | 1 149 562 | 10/2001 |
| EP | 1 201 191 | 5/2002 |
| EP | 1 348 384 | 10/2003 |
| FR | 2 671 006 | 7/1992 |
| FR | 2 802 080 | 6/2001 |
| JP | 11 188043 A | 7/1999 |
| NL | 9001858 | 3/1992 |
| WO | WO9820939 | 5/1998 |
| WO | WO 02/051319 A | 7/2002 |

OTHER PUBLICATIONS pp. 2881, Chapter 52, Campbell's Operative Orthopedics, Edited by S. Terry Canale, vol. 3, Tenth Edition.*

Pat. Abs. of Japan, vol. 1999, No. 12 Oct. 29, 1999.

* cited by examiner

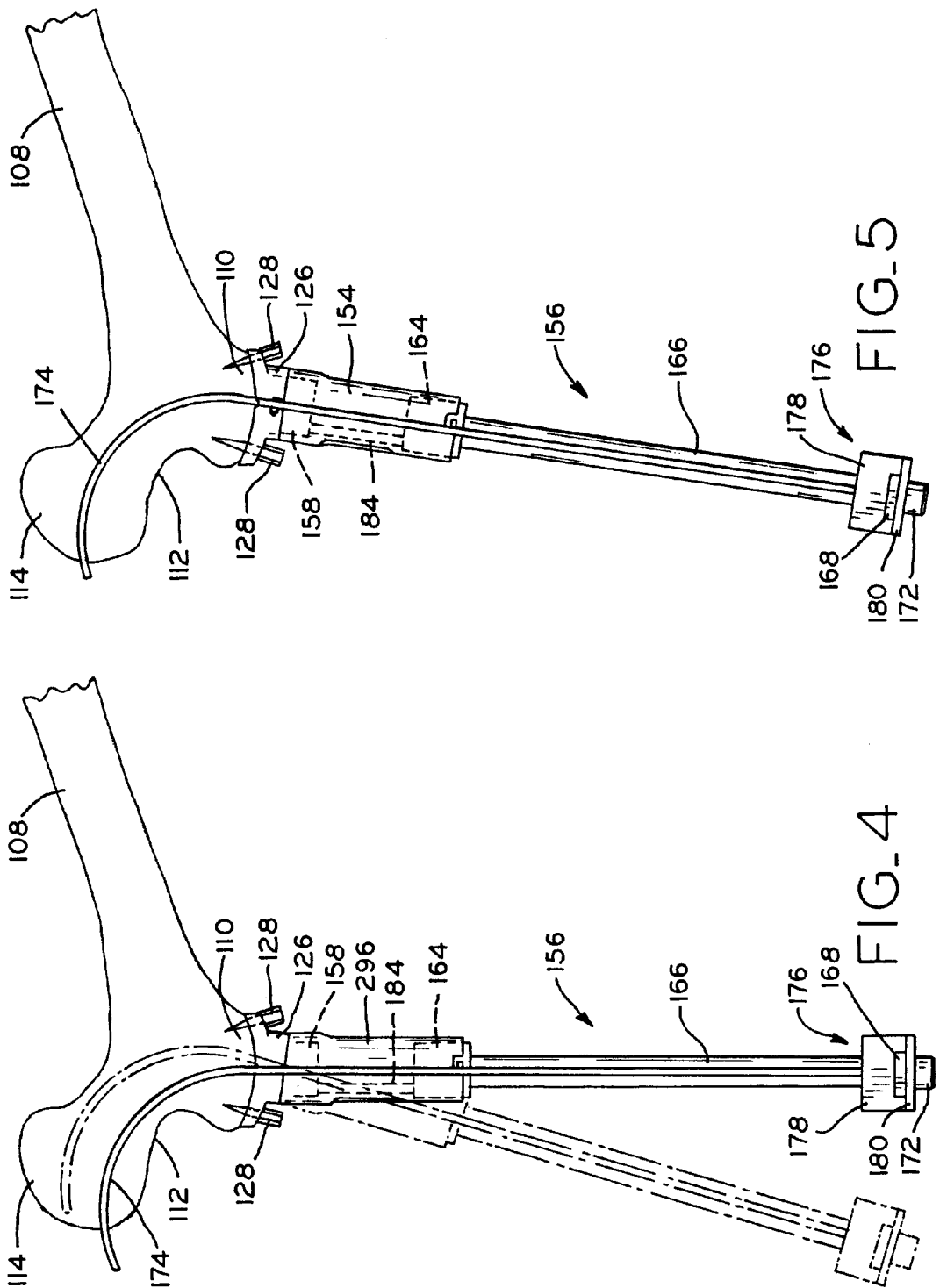

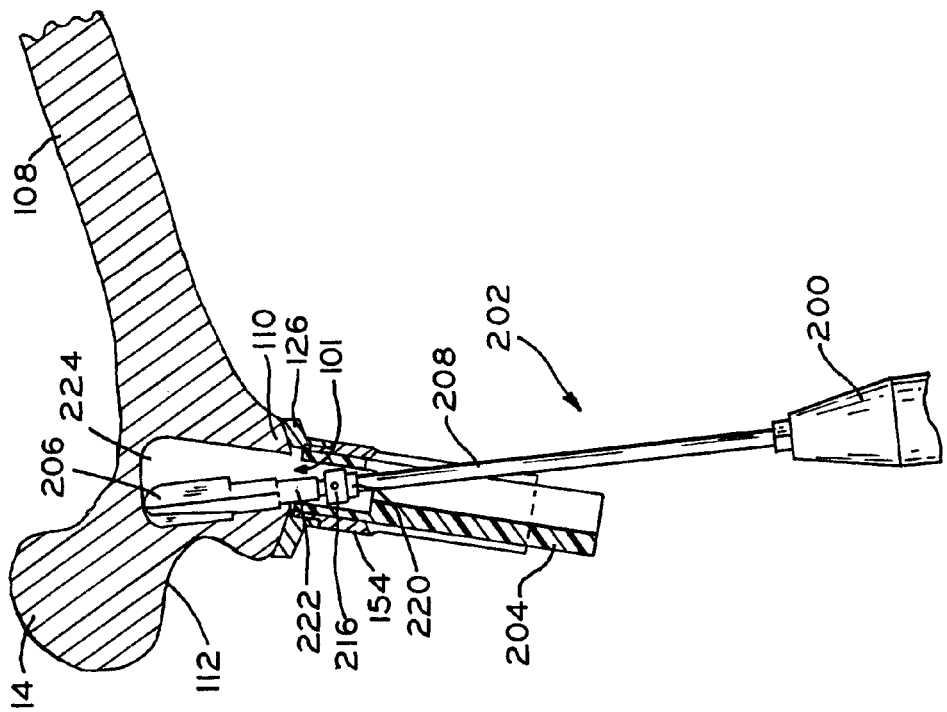
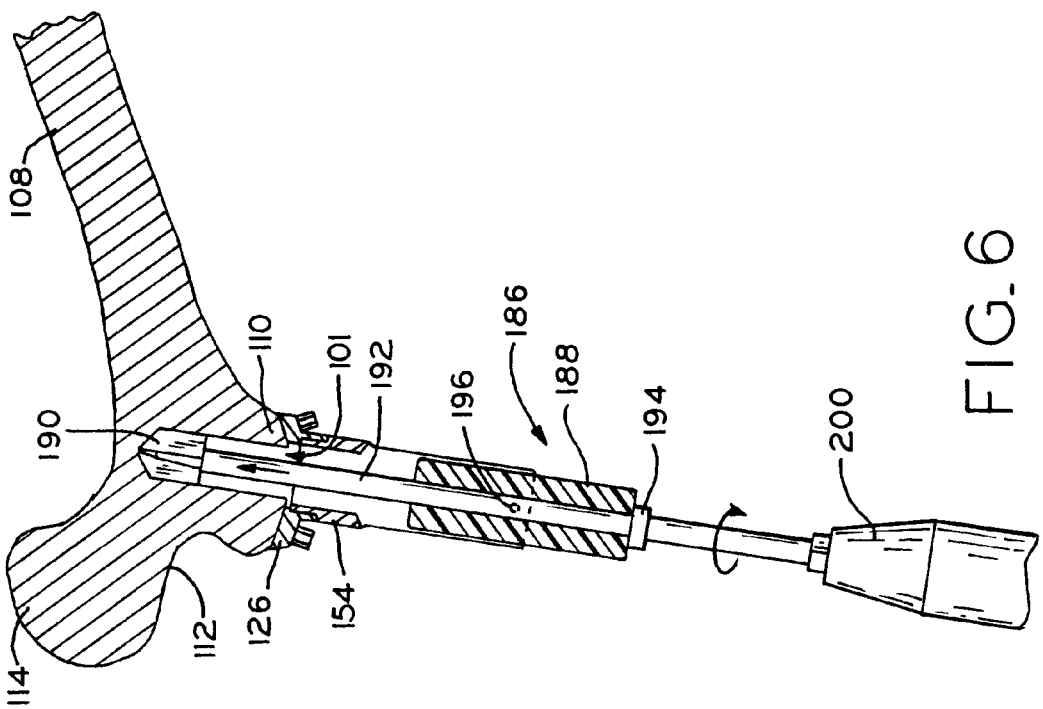

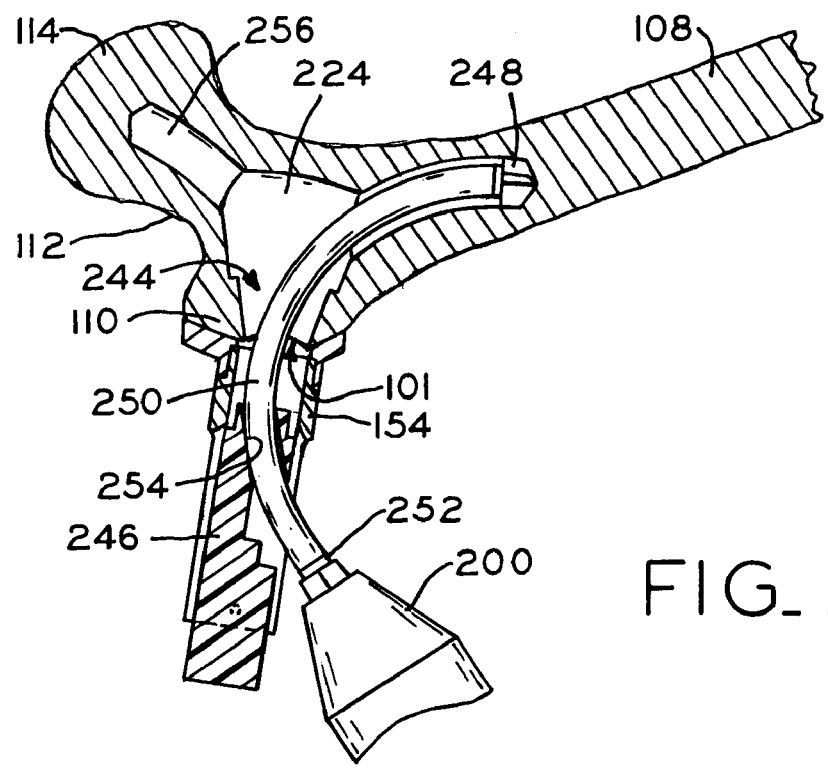
FIG_10
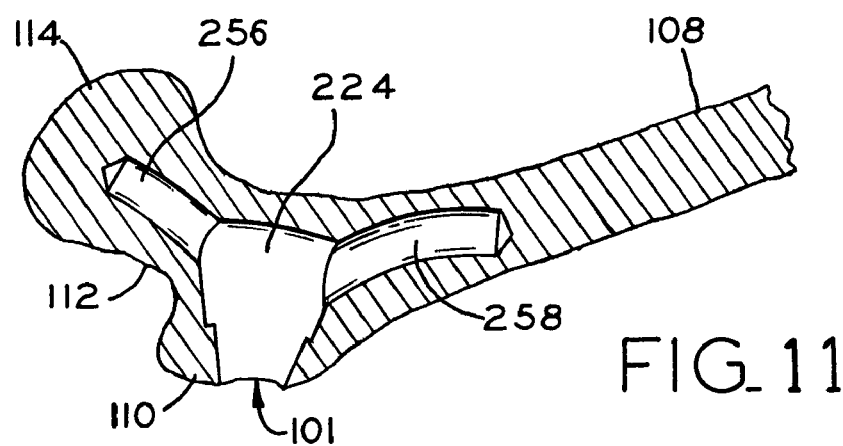
FIG_11

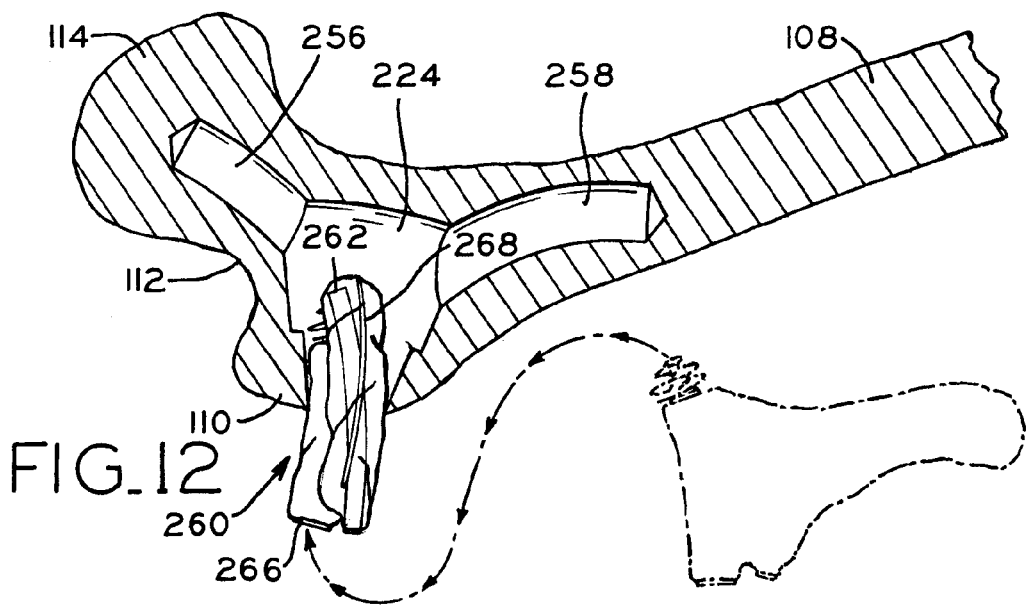
FIG_12
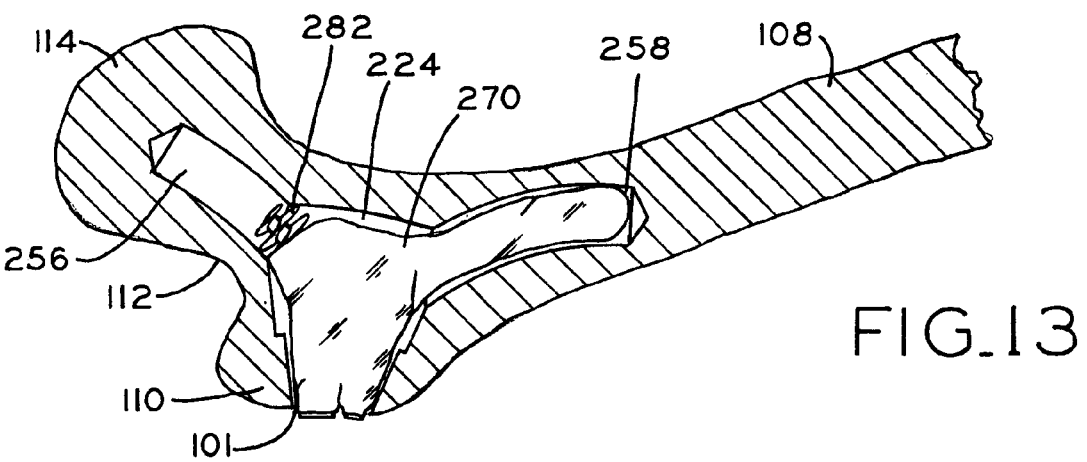
FIG_13
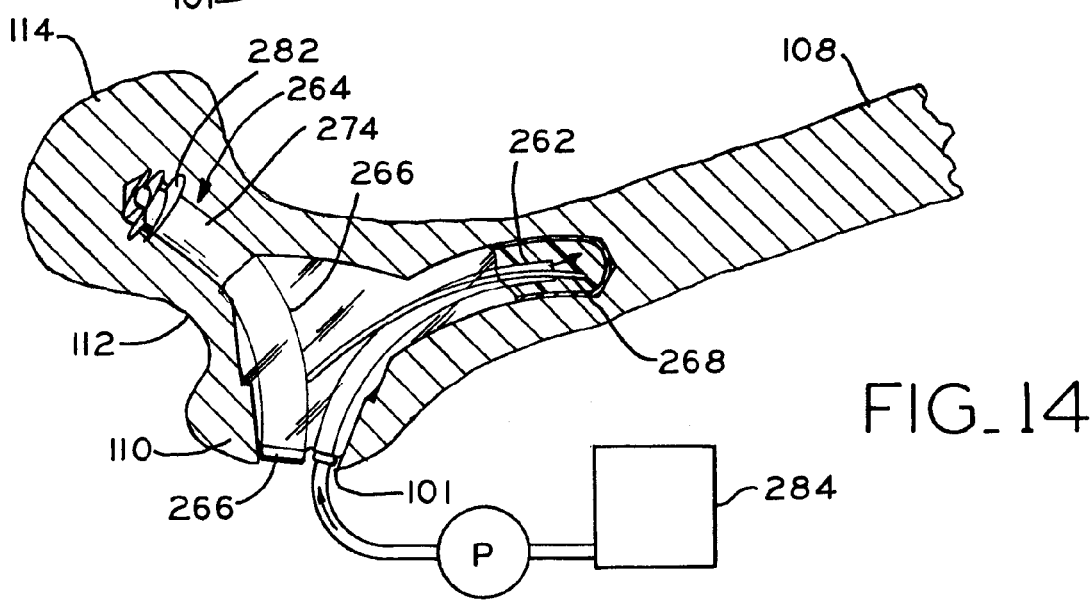
FIG_14

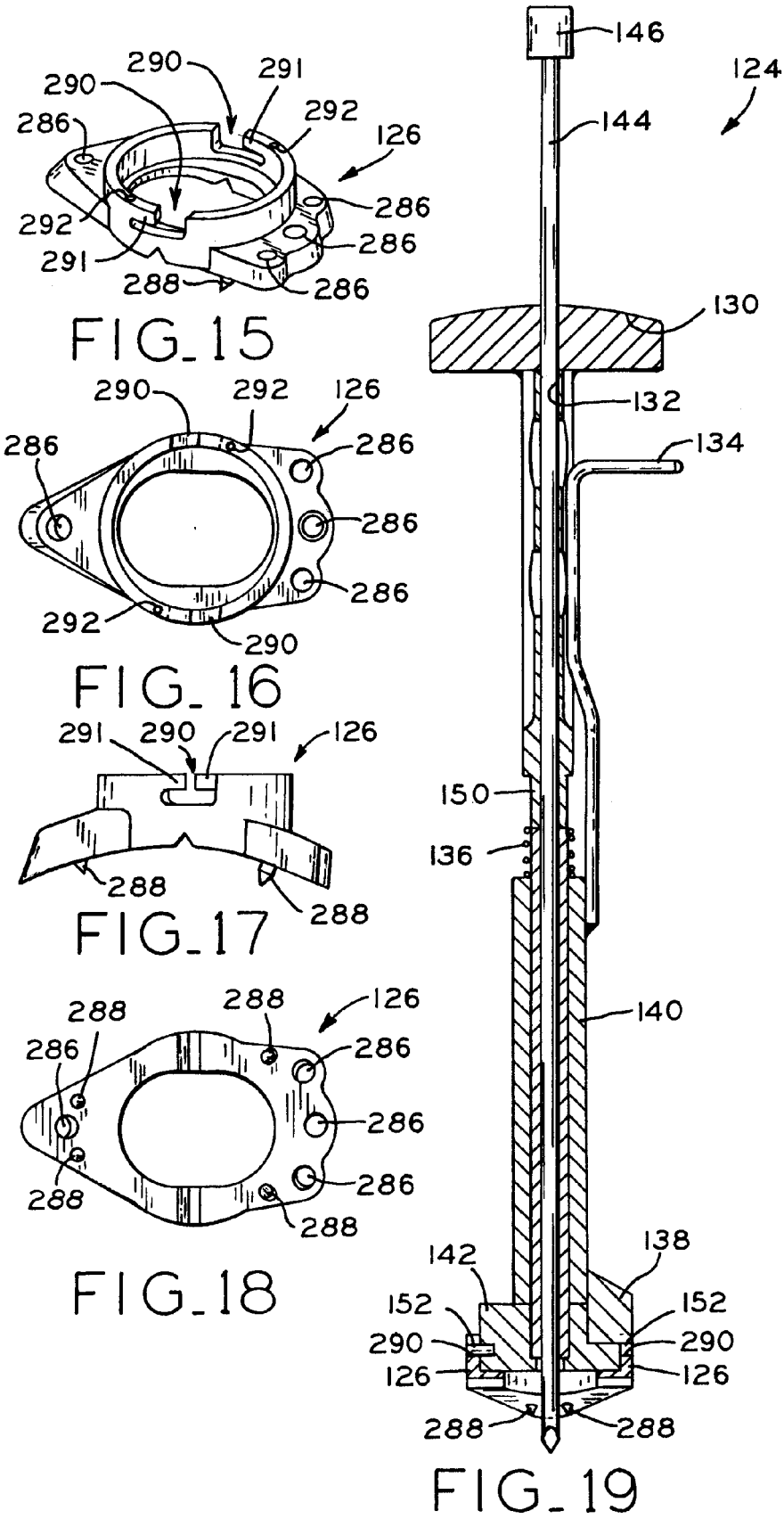

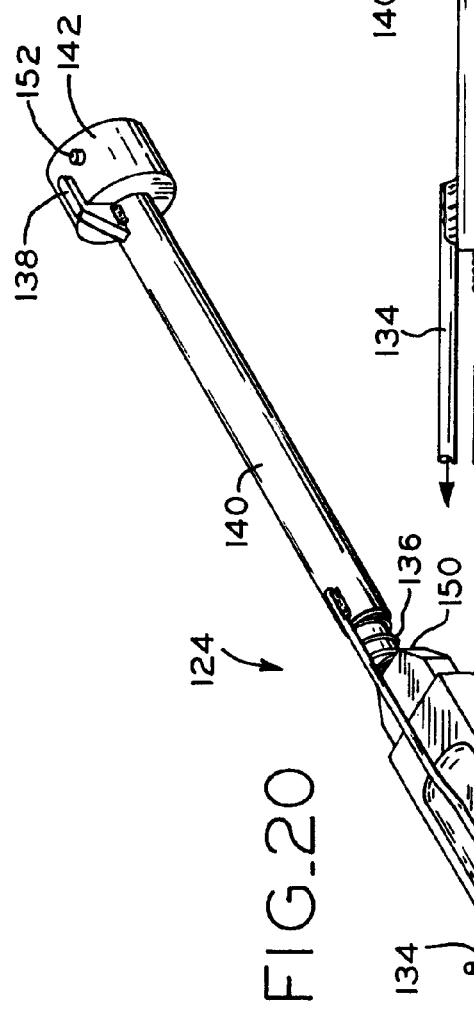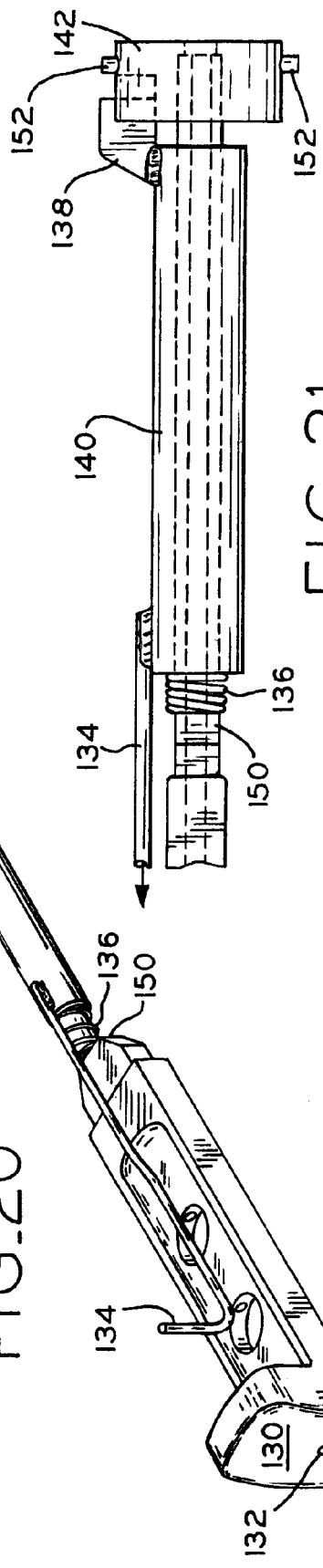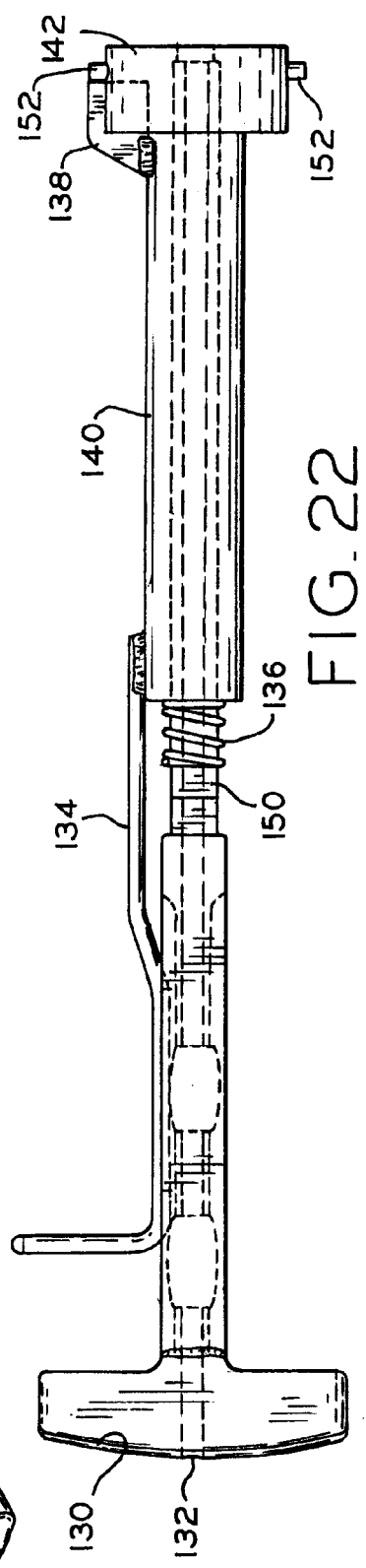

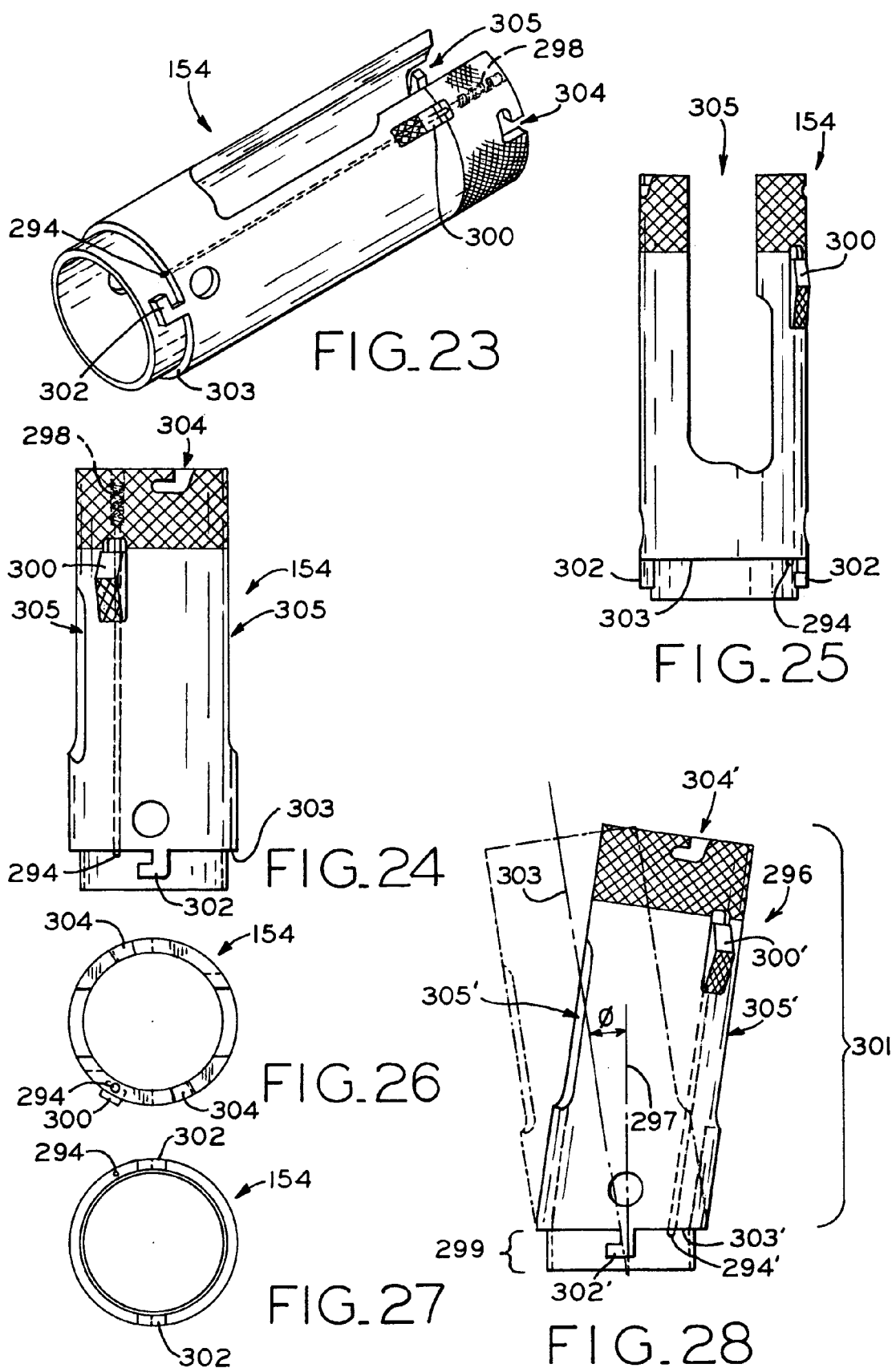

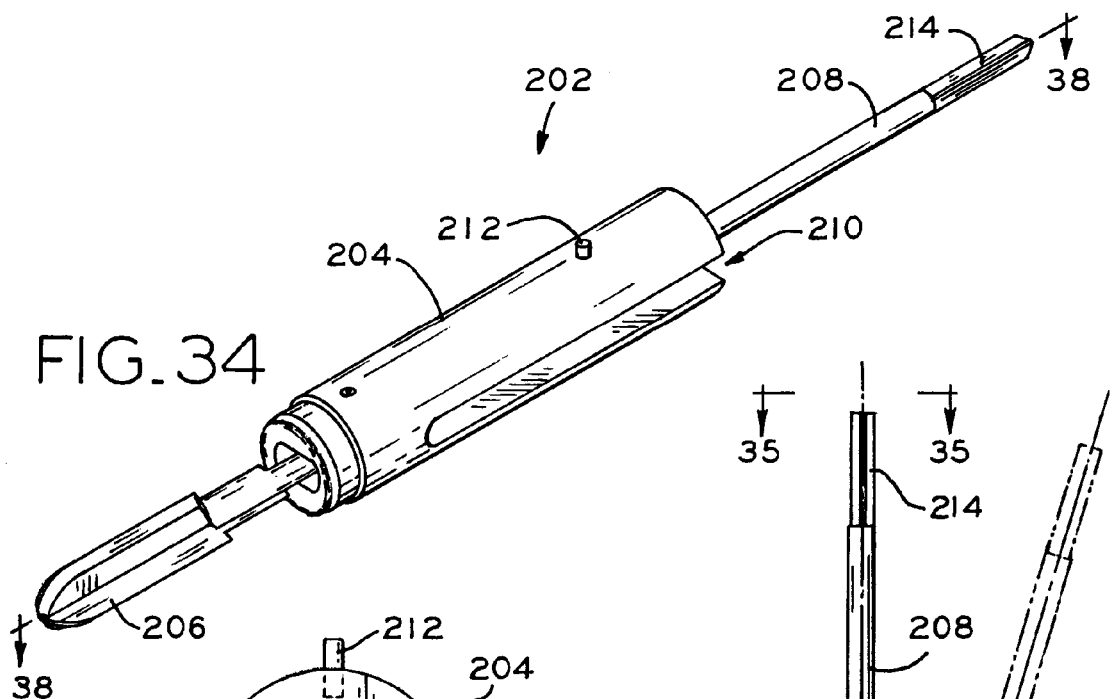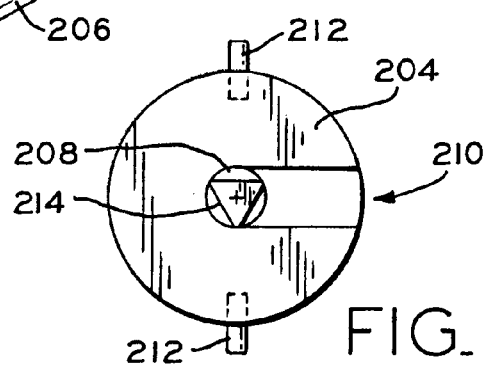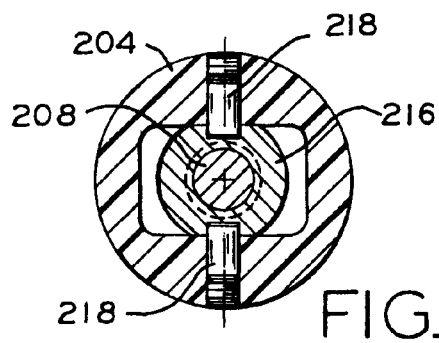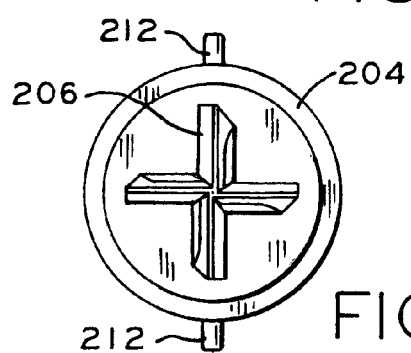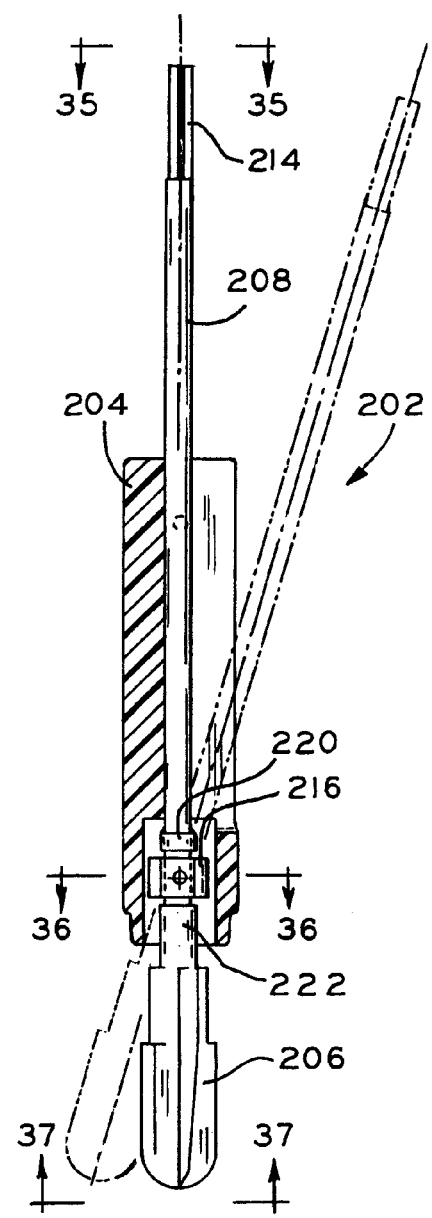
FIG. 34
FIG. 35
FIG. 36
FIG. 37
FIG. 38

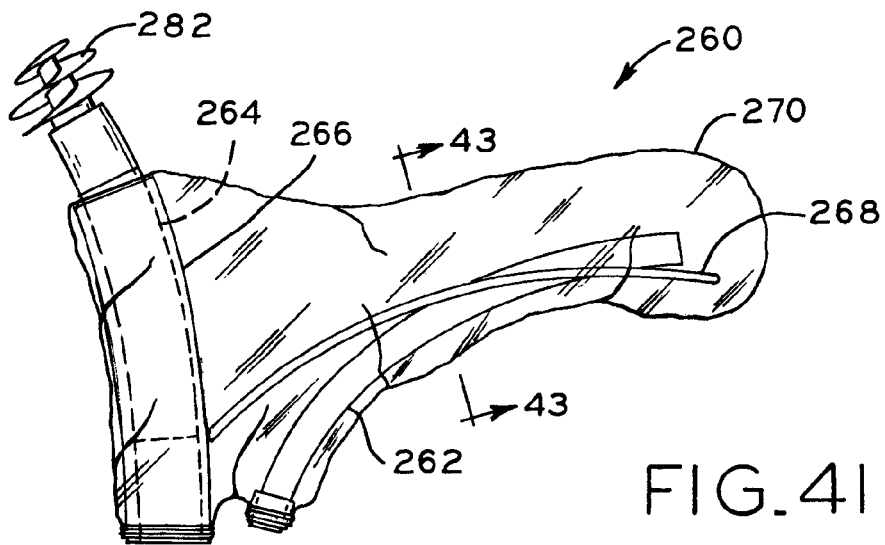
FIG. 41
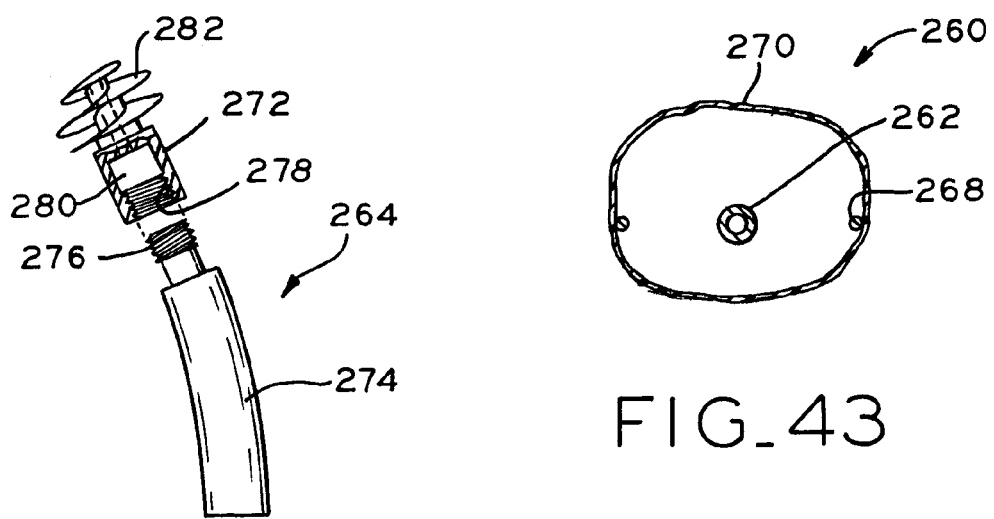
FIG. 42
FIG. 43

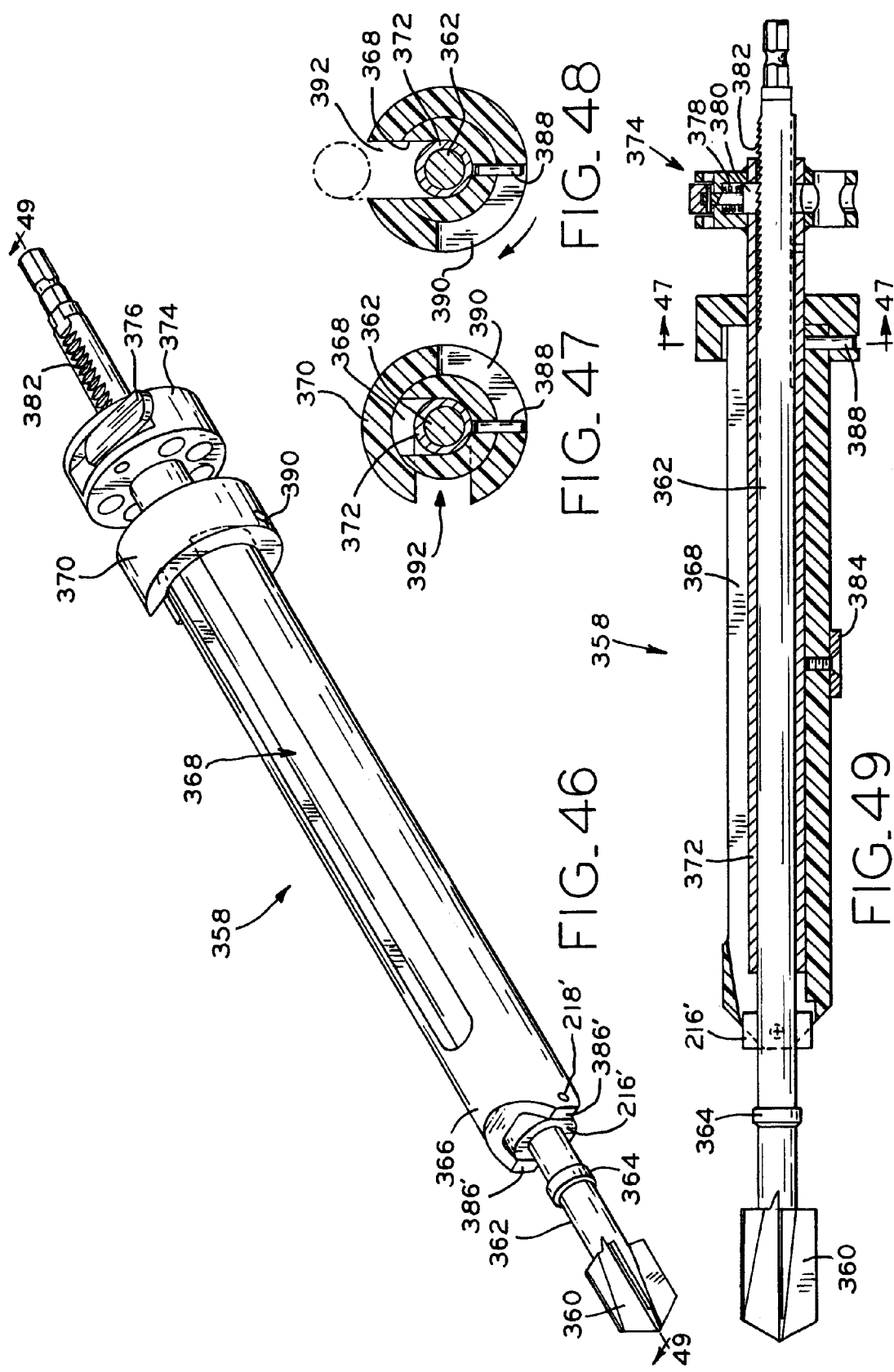

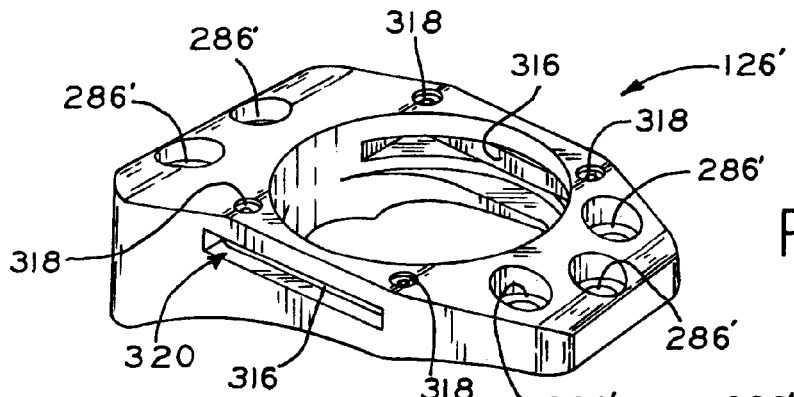
FIG. 50
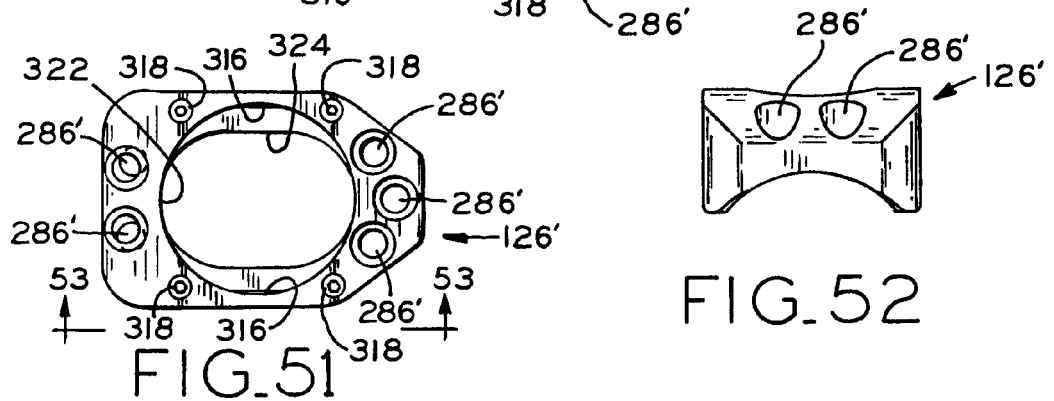
FIG. 51
FIG. 52
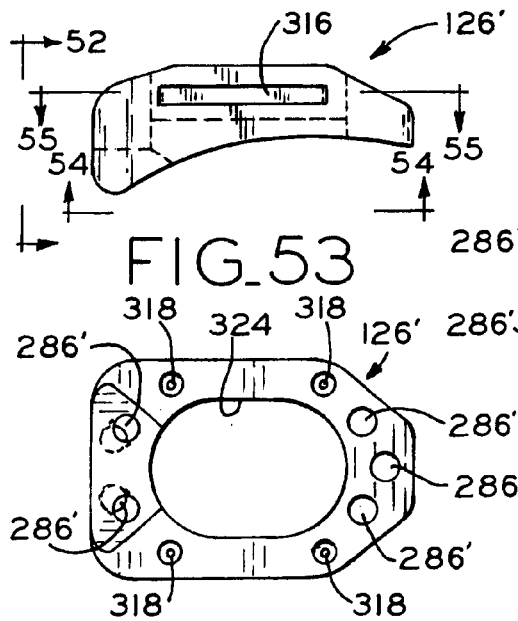
FIG. 53
FIG. 54
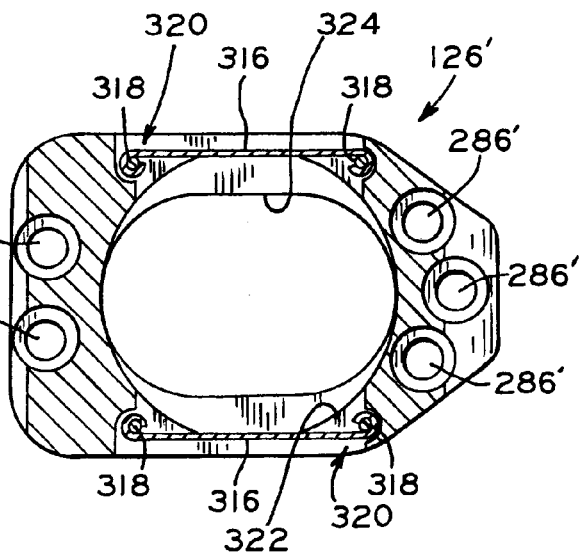
FIG. 55

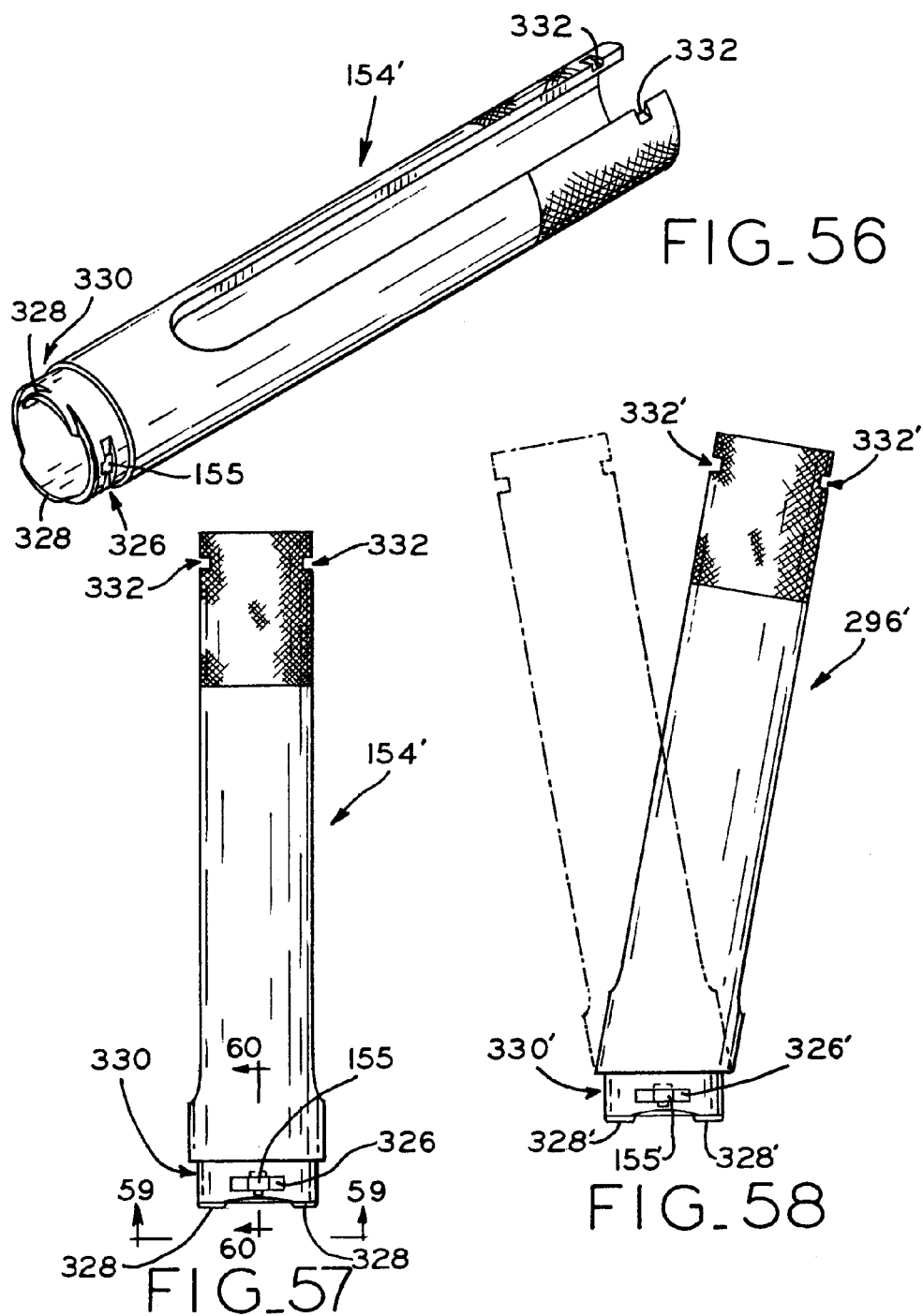

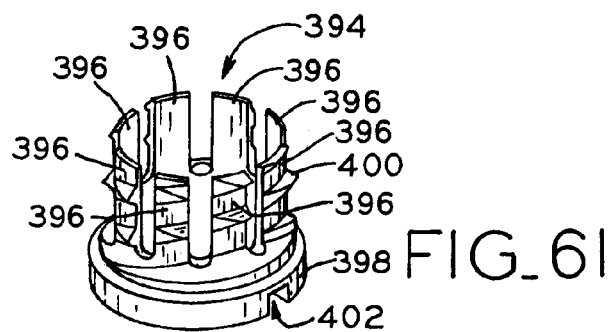
FIG_61
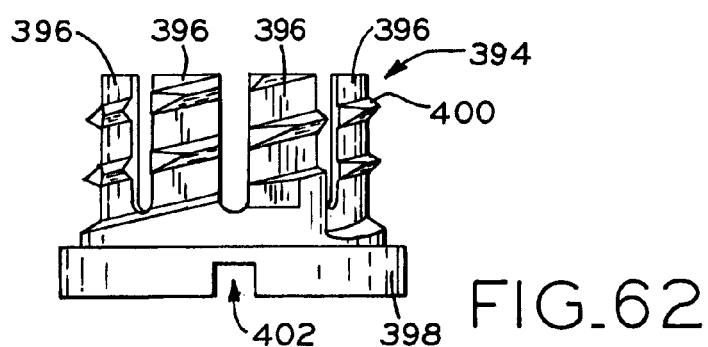
FIG_62
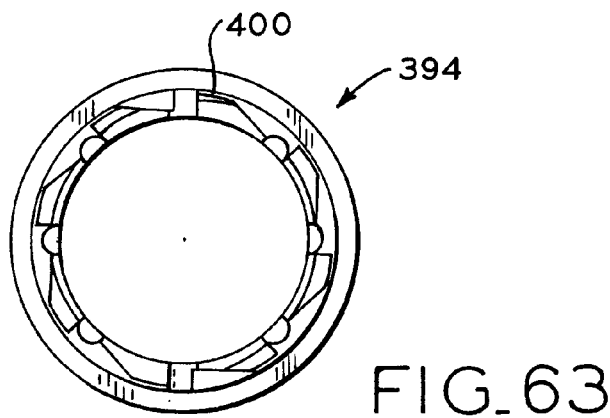
FIG_63
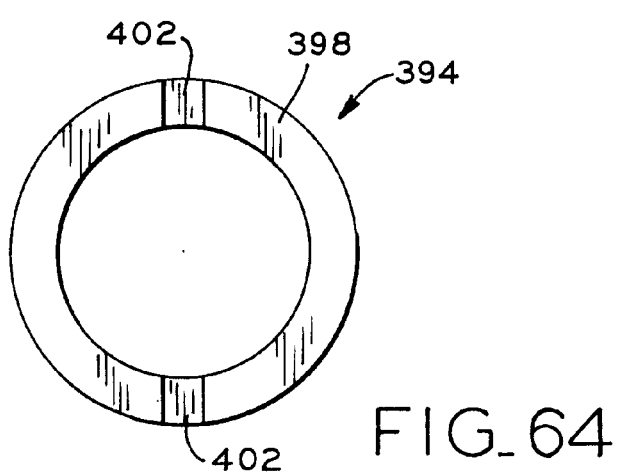
FIG_64

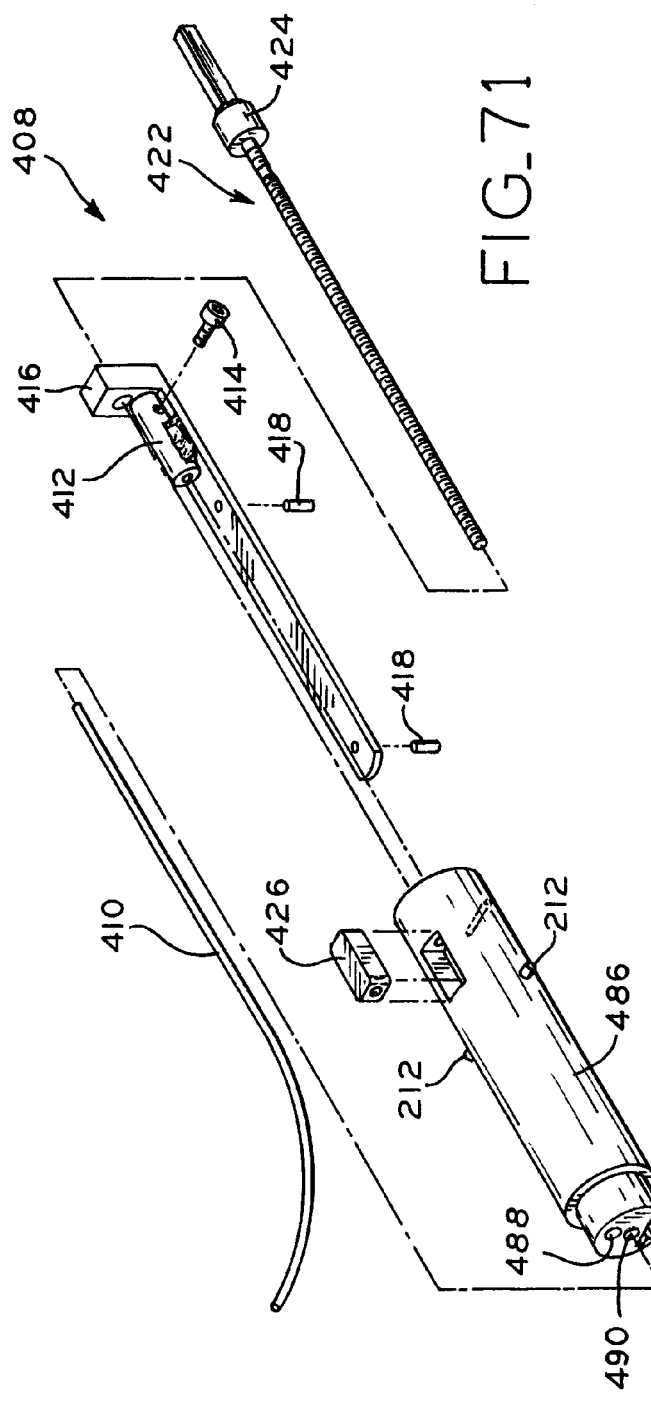
FIG._71
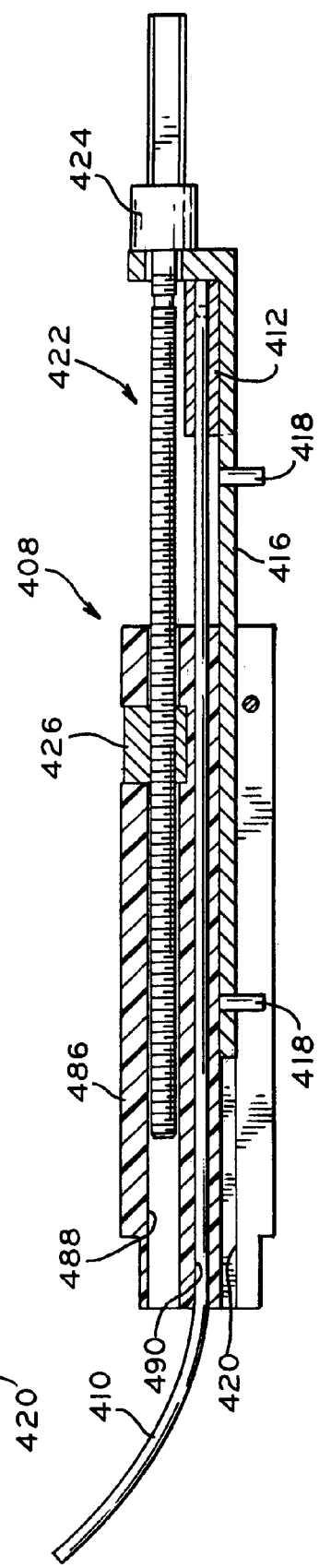
FIG._72

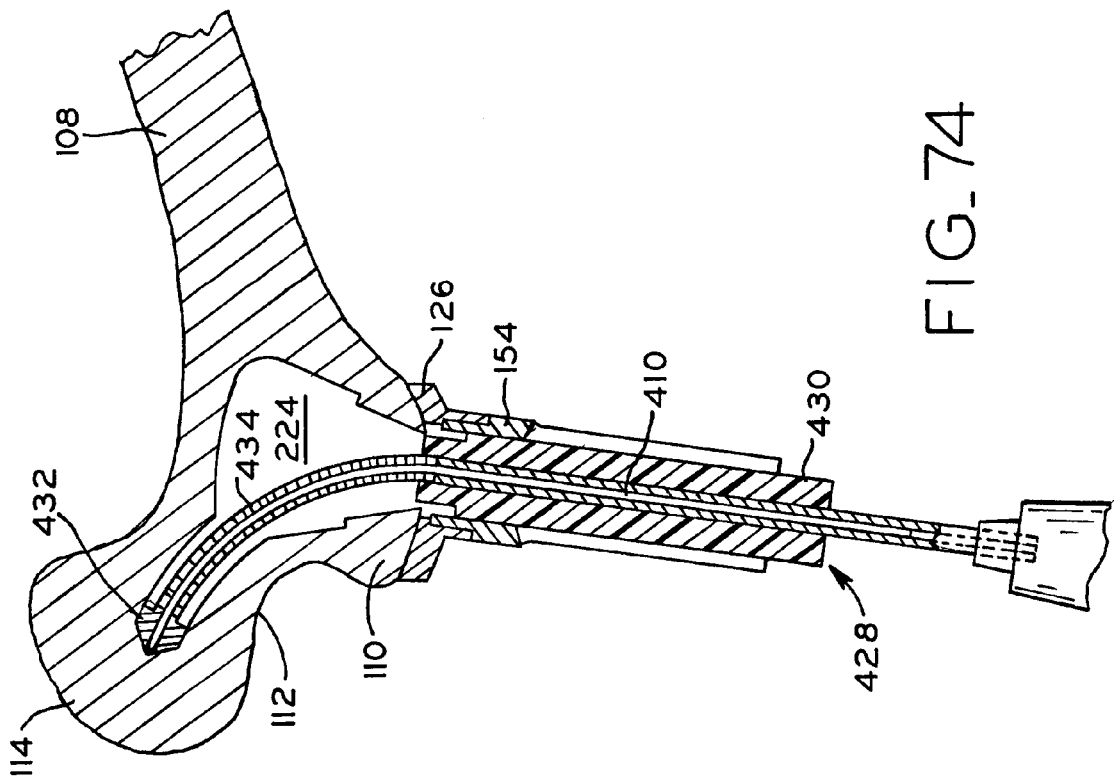
FIG._74
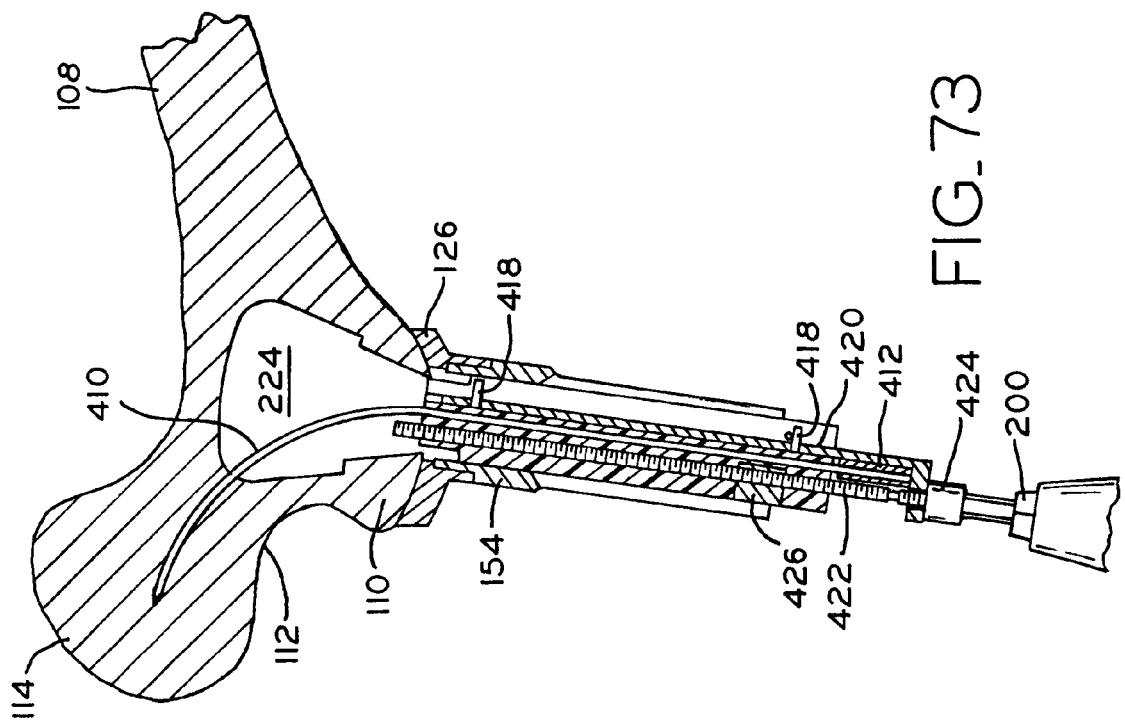
FIG._73

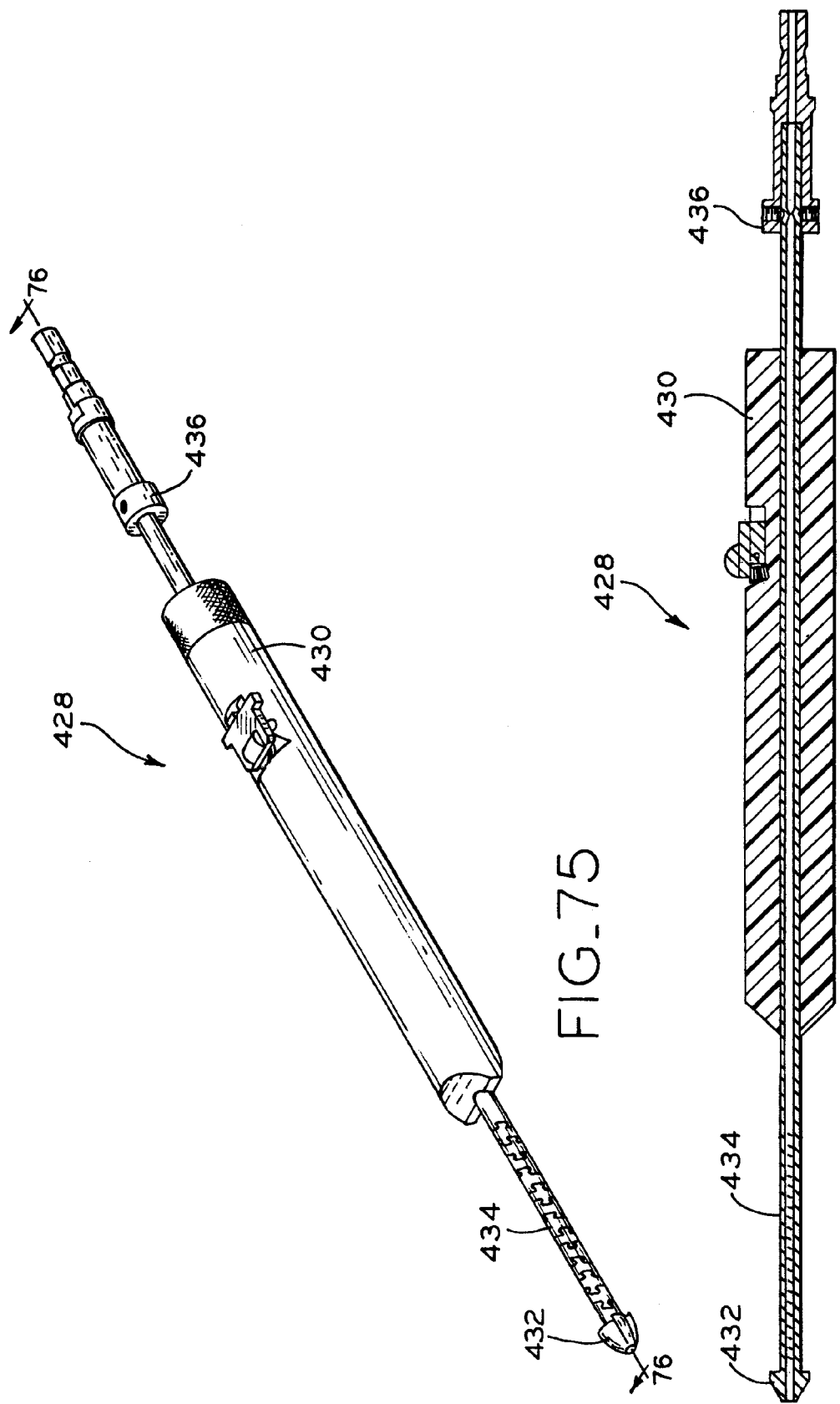

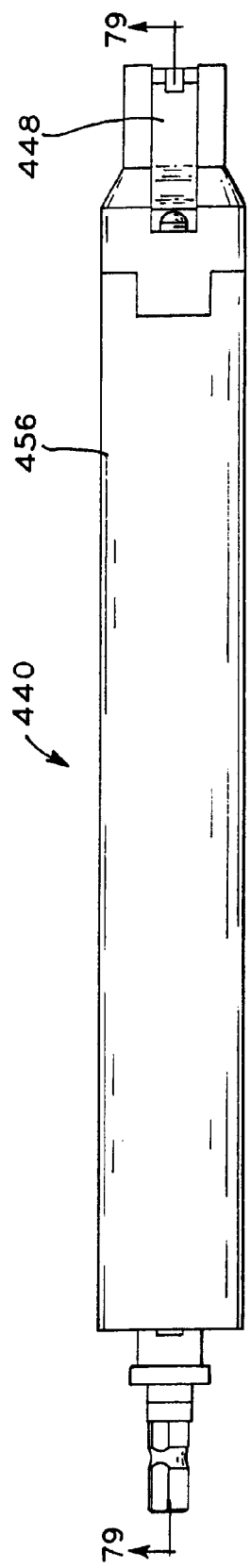
FIG._78
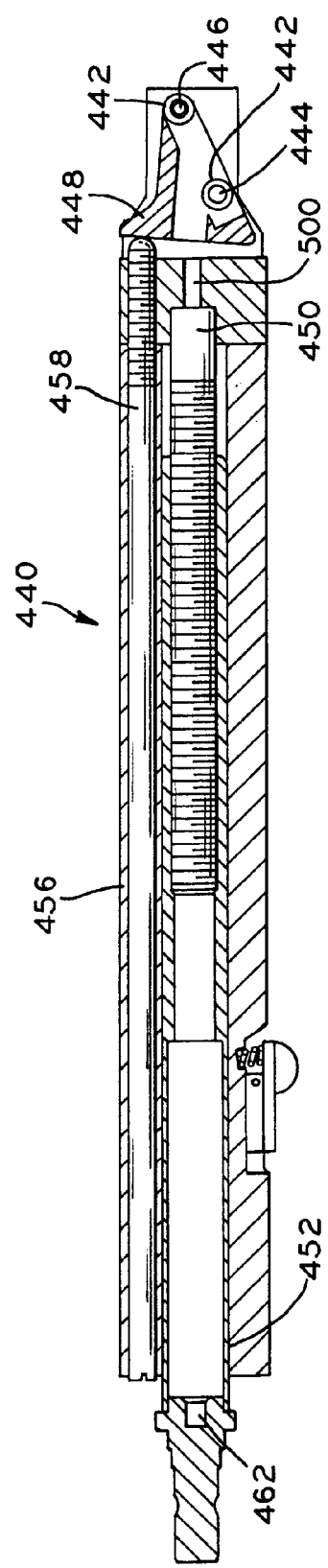
FIG._79

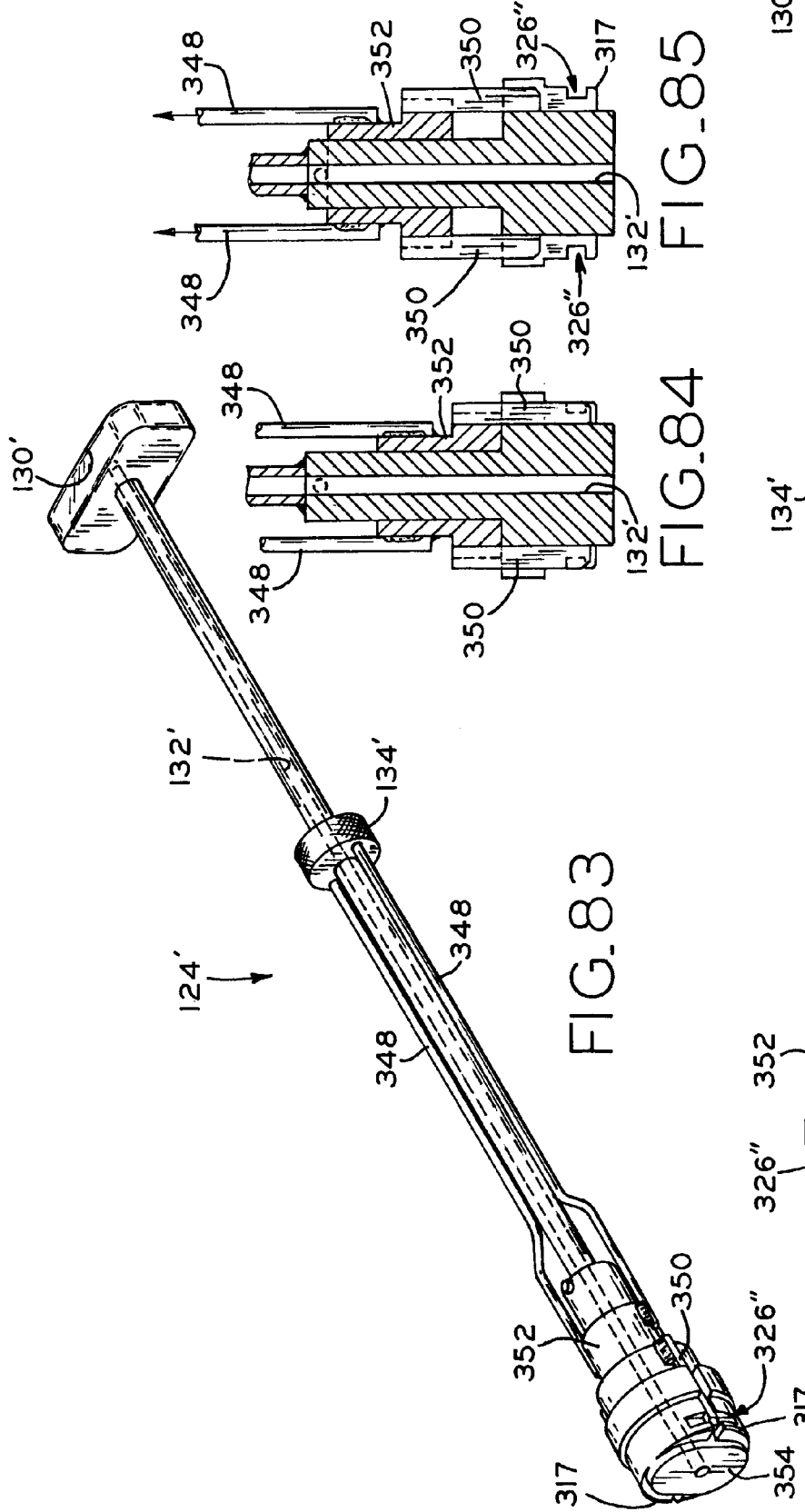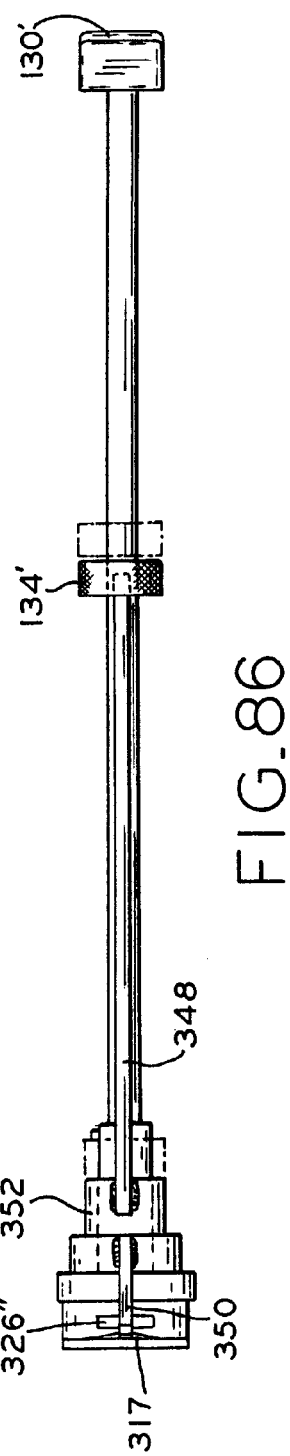

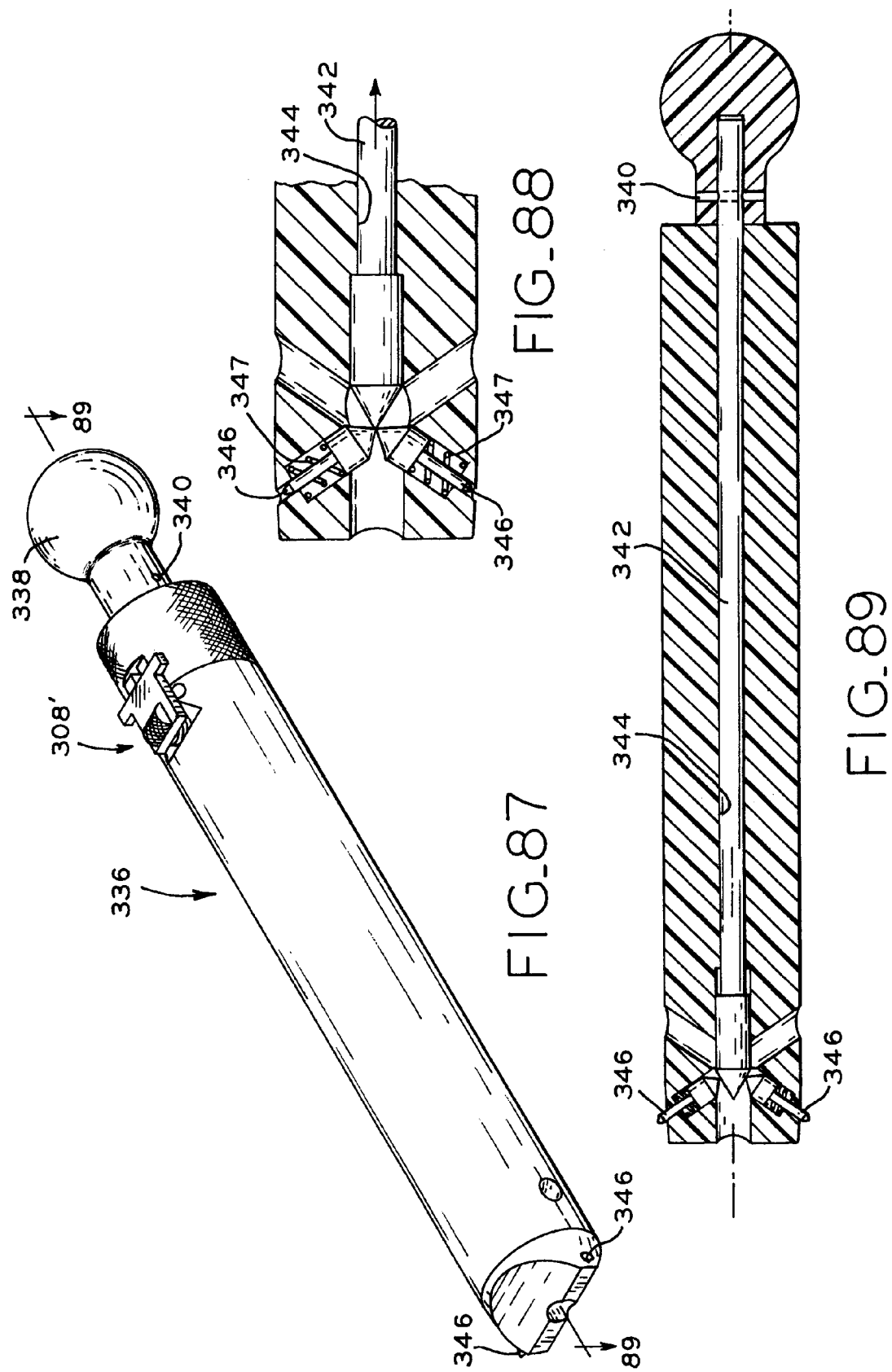

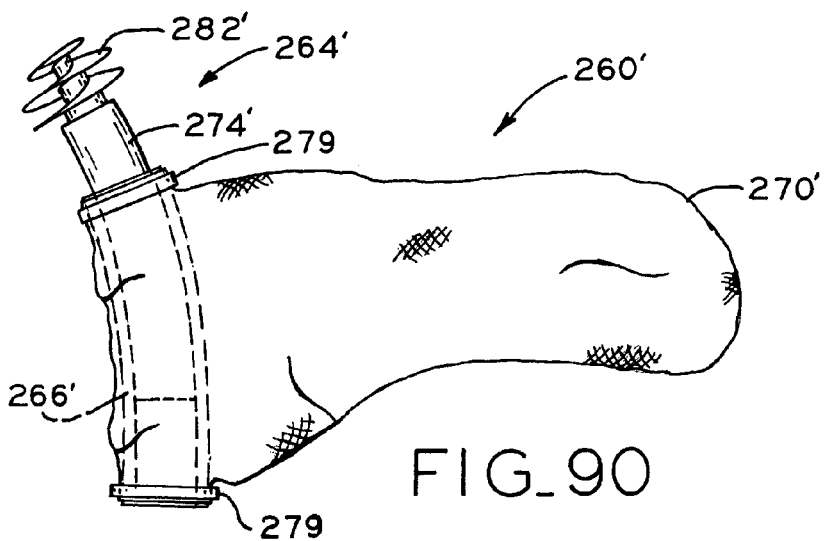
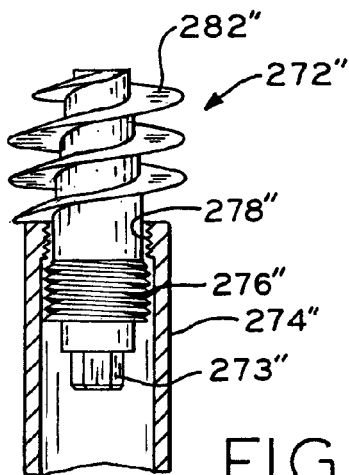
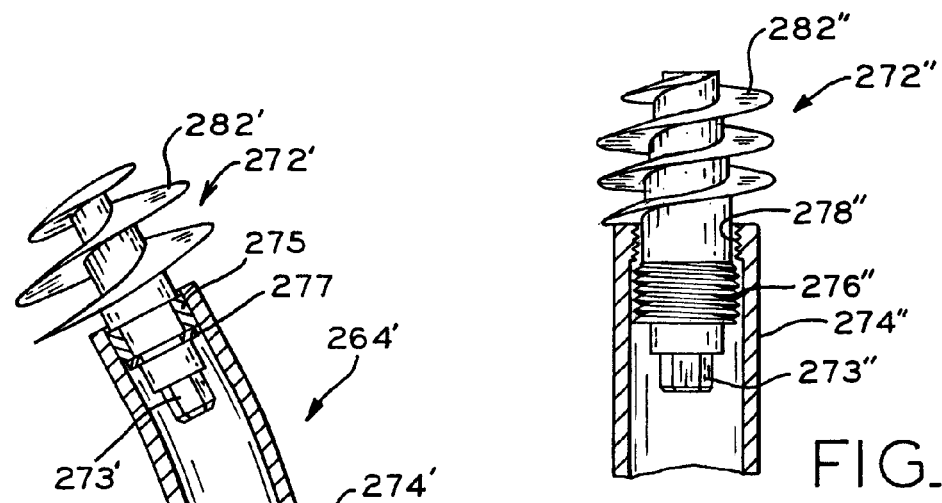
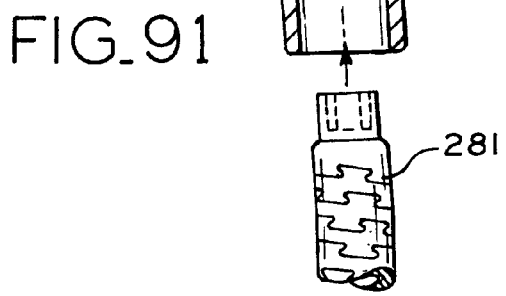

METHOD AND APPARATUS FOR REDUCING FEMORAL FRACTURES

This application is a continuation-in-part of prior U.S. patent application Ser. No. 09/520,351, filed Mar. 7, 2000, now U.S. Pat. No. 6,447,514.

BACKGROUND OF THE INVENTION

1. Field of the Invention

The present invention relates to a method and apparatus for treating hip fractures, and, more particularly, to a method and apparatus for reducing femoral fractures utilizing a minimally invasive procedure.

2. Description of the Related Art

Current procedures utilized to reduce hip fractures generally utilize a side plate/hip screw combination, i.e., a bone plate affixed to a lateral aspect of the femur and having a hip screw operably connected thereto, with the hip screw extending into the femoral head. To properly implant a side plate hip screw, a surgeon must dissect an amount of muscle to expose the femur and operably attach the bone plate and hip screw. Typically, the side plate hip screw requires an incision of about 10-12 cm through the quadriceps to expose the femur. While this approach provides surgeons with an excellent view of the bone surface, the underlying damage to soft tissue, including muscle, e.g., the quadriceps can lengthen a patient's rehabilitation time after surgery.

What is needed in the art is a method and apparatus for reducing a hip fracture without requiring incision of soft tissue, including, e.g., the quadriceps.

SUMMARY OF THE INVENTION

The present invention provides an improved method and apparatus for reducing a hip fracture utilizing a minimally invasive procedure which does not require dissection of the quadriceps. A femoral implant in accordance with the present invention achieves intramedullary fixation as well as fixation into the femoral head to allow for the compression needed for a femoral fracture to heal. The femoral implant of the present invention allows for sliding compression of the femoral fracture. To operably position the femoral implant of the present invention, an incision aligned with the greater trochanter is made and the wound is developed to expose the greater trochanter. The size of the wound developed on the surface is substantially constant throughout the depth of the wound. In one exemplary embodiment of the present invention, the incision through which the femur is prepared and the implant is inserted measures about 2.5 centimeters (3.9 inches). Because the greater trochanter is not circumferentially covered with muscle, the incision can be made and the wound developed through the skin and fascia to expose the greater trochanter, without incising muscle, including, e.g., the quadriceps. After exposing the greater trochanter, novel instruments of the present invention are utilized to prepare a cavity in the femur extending from the greater trochanter into the femoral head and further extending from the greater trochanter into the intramedullary canal of the femur. After preparation of the femoral cavity, a femoral implant in accordance with the present invention is inserted into the aforementioned cavity in the femur. The femoral implant is thereafter secured in the femur, with portions of the implant extending into and being secured within the femoral head and portions thereof extending into and being secured within the femoral shaft. To allow for sliding compression, the portion of the implant extending into the femoral head is slidable relative to the portion of the implant extending into the femoral shaft.

The femoral implant of the present invention includes a sealed bag having a fill tube positioned therein to provide access to the bag interior so that the implant bag can be filled with material, e.g., bone cement after implantation of the femoral implant within the cavity formed in the femur. The femoral implant of the present invention further includes a lag screw tube placed within the bag of the femoral implant. The bag of the femoral implant is tightly secured to the exterior of the lag screw tube to prevent material injected into the bag from escaping the bag at any point at which the bag contacts the lag screw tube. The lag screw tube is hollow and accommodates a lag screw or other fixation device to be advanced into and secured to the femoral head. The sealed bag of the femoral implant of the present invention can be, e.g., formed of various films and fabrics. In one exemplary embodiment the bag of the femoral implant of the present invention is formed from an acrylic material. Because bone cement is an acrylic, if the implant bag is formed of an acrylic, the bag and the bone cement will achieve an intimate chemical bond.

In a further embodiment of the present invention, the bag structure of the implant of the present comprises a nested bag structure in which an inner bag is filled with a high strength material relative to an outer bag in which the inner bag is placed. The outer bag of this form of the present invention is formed from and filled with a more bioresorbable material relative to the material of construction and fill material of the inner bag.

The femoral implant of the present invention is inserted through an access aperture formed in the greater trochanter and placed within the femoral cavity described hereinabove. The lag screw or other fixation device is thereafter advanced through the lag screw tube and into the cavity formed in the femoral head. The lag screw or other fixation device is then secured to the femoral head. The fill tube is thereafter utilized to fill the femoral implant with, e.g., bone cement to fill the femoral cavity and provide intramedullary fixation and stabilization of the lag screw. In an alternative embodiment of the present invention, bone cement is utilized in lieu of lag screw threads to secure a lag screw shaft of an implant of the present invention.

Several different guides and reamers may be utilized in accordance with the present invention to ream the femoral cavity described hereinabove. These novel guides and reamers will be described in detail in the detailed description portion of this document. Generally, the guides and reamers of the present invention are designed to allow for formation of a femoral cavity from the greater trochanter across the femoral neck and into the femoral head as well as from the greater trochanter into the intramedullary canal, with the femoral cavity having exposed access thereto only over the greater trochanter The method and apparatus of the current invention advantageously allow for the treatment of a femoral hip fracture in a minimally invasive procedure, which hastens patient recovery.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 4 is an elevational view illustrating the use of an alignment device of the present invention to properly select the appropriate guide tube/retractor of the present invention;

FIG. 5 is an elevational view illustrating the alignment guide of FIG. 4 properly aligned from the greater trochanter along the femoral neck to the femoral head;

FIG. 6 is a sectional view of a femur illustrating a plunge reamer utilized to begin making the femoral cavity of the present invention;

FIG. 7 is a sectional view illustrating the use of a swivel reamer in accordance with the present invention to further form the femoral cavity;

FIG. 10 is a sectional view illustrating the use of a curved femoral reamer to extend the femoral cavity into the intramedullary canal of the femur;

FIG. 11 is a sectional view illustrating a femoral cavity formed in accordance with the present invention;

FIG. 12 is a sectional view illustrating insertion of a femoral implant of the present invention into the femoral cavity illustrated in FIG. 11;

FIG. 13 is a sectional view illustrating extension of the bag of the femoral implant into the intramedullary canal;

FIG. 14 is a sectional view illustrating extension of a lag screw through the lag screw tube and into the femoral head, as well as a pump and source of bag fill, e.g., bone cement, utilized to fill the bag of the femoral implant of the present invention;

FIG. 15 is a perspective view of a guide plate in accordance with the present invention;

FIGS. 16, 17, and 18 are, respectively, top, side, and bottom elevational views thereof;

FIG. 19 is a sectional view of an insertion member of the present invention with the guide plate illustrated in FIGS. 15-18 affixed thereto;

FIG. 20 is a perspective view of an insertion member which is utilized to operably position a guide plate, e.g., the guide plate illustrated in FIGS. 15-18 atop the greater trochanter as illustrated in FIG. 2;

FIG. 21 is a partial elevational view illustrating deactuation of the latch utilized to temporarily fix the guide plate to the insertion member;

FIG. 22 is a side elevational view of the insertion member illustrated, e.g., in FIG. 20;

FIG. 23 is a perspective view of a guide tube/retractor of the present invention;

FIG. 24 is a radial elevational view thereof;

FIG. 25 is a further radial elevational view thereof, rotated approximately 90 degrees with respect to the radial elevational view of FIG. 24;

FIG. 26 is a proximal axial view thereof;

FIG. 27 is a distal axial view thereof;

FIG. 28 is a radial elevational view of an angled guide tube/retractor of the present invention;

FIG. 34 is a perspective view of a swivel reamer of the present invention;

FIG. 35 is a proximal axial elevational view thereof;

FIG. 36 is a sectional view taken along line 36-36 of FIG. 38;

FIG. 37 is a distal axial elevational view thereof;

FIG. 38 is a partial sectional, elevational view of the swivel reamer of the present invention;

FIG. 41 is an elevational view of a femoral implant of the present invention;

FIG. 42 is an exploded view of a lag screw of the present invention;

FIG. 43 is a sectional view of the femoral implant of the present invention taken along line 43-43 of FIG. 41;

FIG. 46 is a perspective view of a combination reamer in accordance with the present invention;

FIG. 47 is a sectional view thereof illustrating actuation of the swivel/plunge reaming selector into the plunge reaming position;

FIG. 48 is a sectional view thereof with the swivel/plunge reaming selector moved into position for swivel reaming;

FIG. 49 is a partial sectional view of the combination reamer of the present invention;

FIG. 50 is a perspective view of an alternative embodiment guide plate in accordance with the present invention;

FIGS. 51-54 are top, end, side, and bottom elevational views thereof, respectively;

FIG. 55 is a sectional view thereof taken along line 55-55 of FIG. 53;

FIG. 56 is a perspective view of an alternative embodiment guide tube/retractor of the present invention;

FIG. 57 is a radial elevational view thereof;

FIG. 58 is a radial elevational view of an alternative embodiment angled guide tube/retractor of the present invention;

FIG. 59 is a distal axial elevational view of the guide tube/retractor illustrated in FIG. 57;

FIG. 60 is a partial sectional view of the guide tube/retractor illustrated in FIG. 57 taken along line 60-60 thereof;

FIG. 61 is a perspective view of a fixation screw in accordance with an alternative embodiment of the present invention;

FIG. 62 is a radial elevational view thereof,

FIG. 63 is a distal axial view thereof;

FIG. 64 is a proximal axial view thereof;

FIG. 71 is an exploded view of a flexible reamer guide in accordance with the present invention;

FIG. 72 is a sectional view thereof;

FIG. 73 is a sectional view illustrating the flexible reamer guide of FIGS. 71 and 72 operably positioned within a patient's femur to guide a flexible reamer into the femoral head;

FIG. 74 is a sectional view illustrating a flexible reamer positioned over a flexible reamer guide wire for reaming into the femoral head;

FIG. 75 is a perspective view of a flexible reamer in accordance with the present invention;

FIG. 76 is a sectional view thereof;

FIG. 78 is an elevational view thereof;

FIG. 79 is a sectional view thereof;

FIG. 83 is a perspective view of an alternative embodiment insertion member for inserting a guide plate of the present invention;

FIG. 84 is a partial sectional view thereof illustrating the release bars thereof actuated to effect release of the guide plate from locking engagement with the insertion member;

FIG. 85 is a partial sectional view illustrating the release bars of the insertion member illustrated in FIG. 83 positioned whereby the guide plate can be temporarily fixed to the insertion member;

FIG. 86 is an elevational view of the insertion member illustrated in FIG. 83;

FIG. 87 is a perspective view of a spring lock release instrument in accordance with the present invention;

FIG. 88 is a partial sectional view of the distal end thereof, illustrating the release pins in an unactuated position;

FIG. 89 is a sectional view of the spring lock release instrument of FIG. 87 actuated to force release pins 346 to protrude therefrom;

FIG. 90 is an elevational view of an alternative embodiment femoral implant of the present invention;

FIG. 91 is a sectional view of an alternative embodiment lag screw of the present invention, illustrating insertion of an actuating device for actuating the lag screw head; and FIG. 92 is a partial sectional view of a further alternative embodiment lag screw of the present invention.

Figure 1:
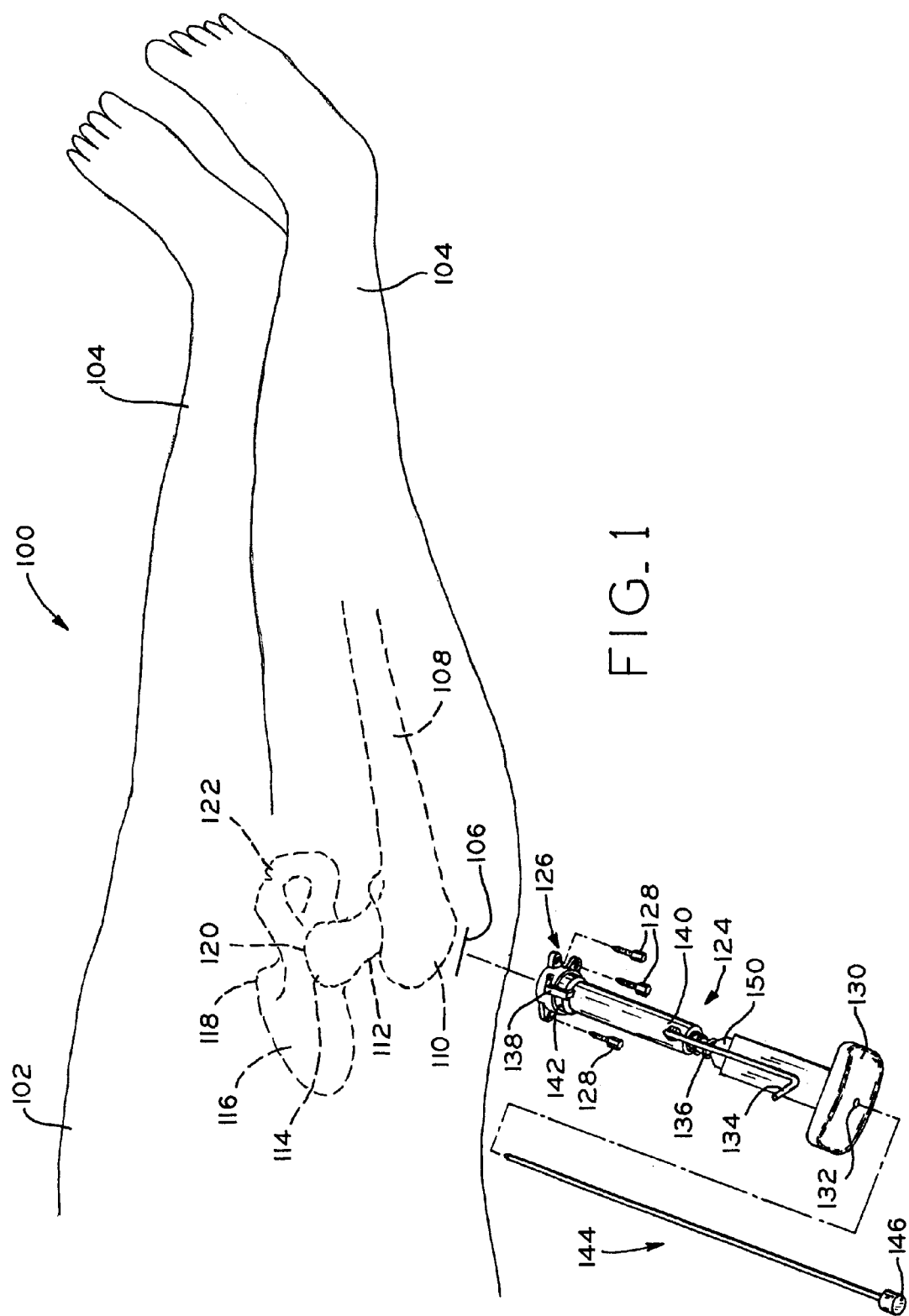
FIG. 1 is a partial perspective view of a patient, with an incision made along the greater trochanter to allow for implantation of a femoral implant of the present invention.

Corresponding reference characters indicate corresponding parts throughout the several views. Although the drawings represent embodiments of the present invention, the drawings are not necessarily to scale and certain features may be exaggerated to better illustrate and explain the present invention. The exemplifications set out herein illustrate embodiments of the invention, and such exemplifications are not to be construed as limiting the scope of the invention in any manner.

DETAILED DESCRIPTION OF THE INVENTION

Implant 260 illustrated in FIG. 41 is utilized to reduce a femoral fracture utilizing a method of implantation which does not require incision of the quadriceps. As illustrated in FIG. 1, incision 106 is aligned with greater trochanter 110, with femur 108 being prepared to receive implant 260 through incision 106. As described above, greater trochanter 110 is not covered with muscle and therefore, incision 106 can be developed to expose greater trochanter 110 without requiring the incision of muscle. As illustrated in FIGS. 6-10, various novel reamers of the present invention are utilized to form femoral cavity 224 (FIG. 11). As illustrated in FIG. 12, implant 260 (further illustrated in FIGS. 41-43) is inserted into femoral cavity 224 via an access formed through greater trochanter 110. As illustrated in FIG. 13, lag screw 264 is advanced into femoral head 114 until lag screw threads 282 firmly engage femoral head 114 and lag screw 264 has achieved the position illustrated in FIG. 14. Bag 270 is thereafter filled with material, e.g., bone cement to fill femoral cavity 224 and provide intramedullary fixation of implant 260 and stabilization of lag screw 264. In this way, a femoral fracture including, e.g., an intertrochanteric fracture can be reduced. Generally, this document will refer to a femoral fracture and, specifically, to an intertrochanteric fracture. However, the method and apparatus of the present invention is adaptable to various bone fractures including, e.g., supracondylar fractures of the femur.

FIG. 1 generally illustrates patient 100 including torso 102, and legs 104. FIG. 1 further illustrates the general bone structures comprising the hip joint including, pubis 122, anterior superior iliac spine 118, ilium 116, acetabulum 120, and femur 108. As illustrated in FIG. 1, femur 108 includes, e.g., greater trochanter 110, femoral neck 112, and femoral head 114. As described above, incision 106 is aligned with greater trochanter 110. Because greater trochanter 110 is not covered with muscle, incision 106 can be made and the wound developed through the skin and fascia to expose greater trochanter 110 without incising muscle, including, e.g., the quadriceps.

Figure 2:
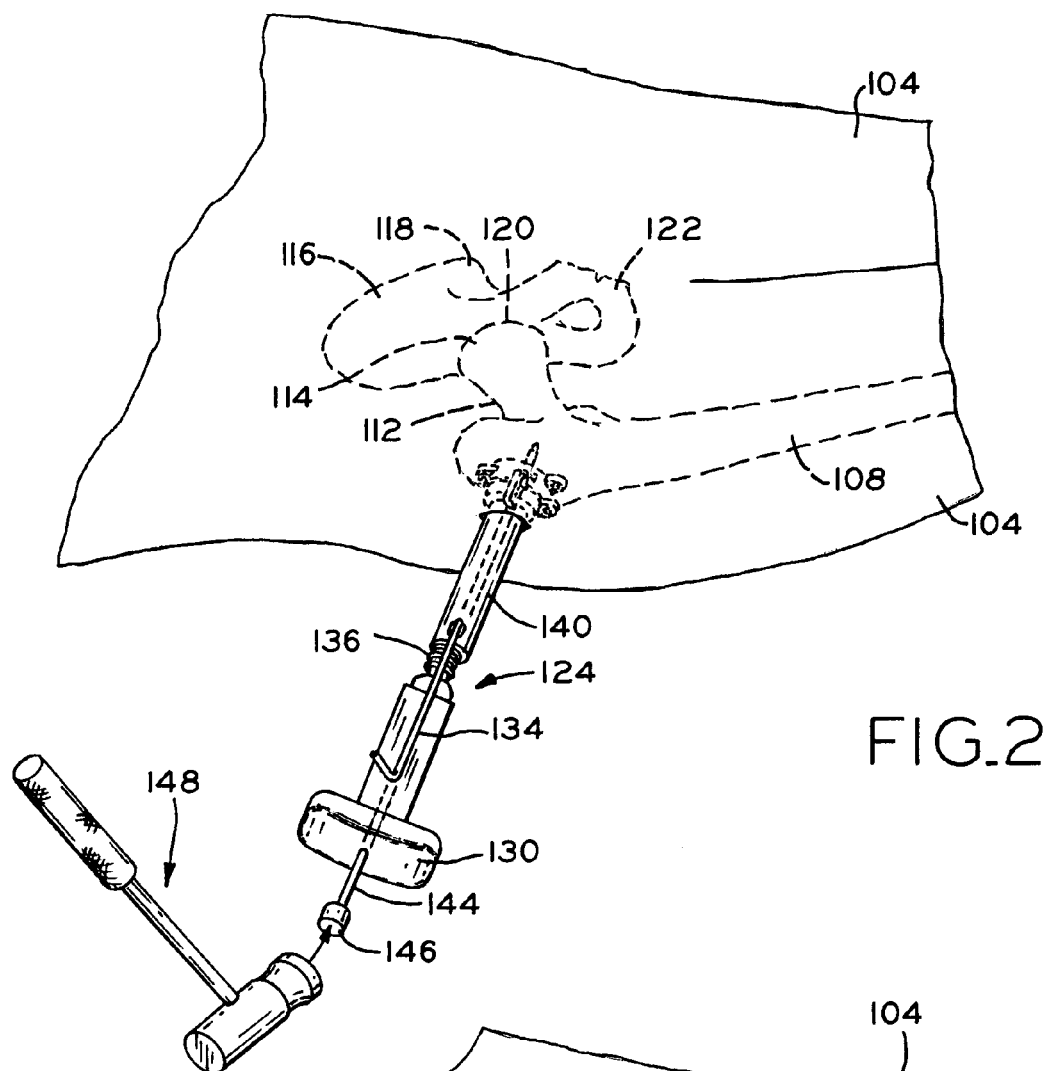
FIG. 2 is a partial perspective view illustrating insertion of a guide plate in accordance with the present invention.

After making incision 106 as illustrated in FIG. 1, cannulated insertion member 124 is utilized to insert guide plate 126 through incision 106 to be placed atop and secured to greater trochanter 110 as illustrated, e.g., in FIG. 2. After guide plate 126 traverses incision 106 and is placed atop greater trochanter 110, stabilization nail 144 is positioned through elongate aperture 132 of insertion member 124 and impaction instrument 148 (FIG. 2) is utilized to strike impaction surface 146 to drive stabilization nail 144 into femur 108 to provide initial stability to guide plate 126 prior to utilizing screws 128 (FIG. 1) to fix guide plate 126 to greater trochanter 110. In one exemplary embodiment, the surgeon implanting guide plate 126 will utilize a fluoroscope to verify proper placement of guide plate 126 atop greater trochanter 110. In alternative embodiments, the surgeon implanting guide plate 126 will utilize tactile feedback either alone or in conjunction with a fluoroscope image to determine proper placement of guide plate 126 atop greater trochanter 110. After guide plate 126 is properly positioned atop greater trochanter 110, screws 128 are driven through corresponding screw apertures 286 (FIG. 15) in guide plate 126 and into femur 108 to secure guide plate 126 to femur 108. Screw apertures 286 are, in an exemplary embodiment, formed in guide plate 126 to allow for oblique insertion of screws 128 relative to guide plate 126.

Insertion member 124 is illustrated in detail in FIGS. 19-22. As illustrated, insertion member 124 includes elongate aperture 132 accommodating stabilization nail 144 as described hereinabove. Insertion member 124 includes tubular latch connector 140 positioned about the distal end thereof. Intermediate the main body of insertion member 124 and tubular latch connector 140 is positioned spring 136. Spring 136 acts against spring stop 150 to bias tubular latch connector into the position illustrated in FIG. 22. Release member 134 is connected to tubular latch connector 140 and is operable to facilitate movement of tubular latch connector 140 against the biasing force of spring 136 into the position illustrated in FIG. 21. Insertion member 124 includes distal end 142 for engaging guide plate 126. Distal end 142 includes bosses 152 extending therefrom.

Guide plate 126 is temporarily affixed to insertion member 124 as described below. Bosses 152 enter attachment channels 290 of guide plate 126 (see, e.g., FIGS. 15 and 17). Concurrently latch 138, connected to tubular latch connector 140, acts against the proximal surface of guide plate 126 to force tubular latch connector 140 against the biasing force of spring 136 and into the position illustrated in FIG. 21. Distal end 142 of insertion member 124 is then rotated until bosses 152 are positioned under lips 291 formed by attachment channels 290 and latch 138 can be positioned within one of attachment channels 290 and returned to its naturally biased position as illustrated in FIGS. 19 and 22. When guide plate 126 is attached to insertion member 124, one of bosses 152 and latch 138 abut opposing radial extremes of one attachment channel 290 to prevent relative rotation of guide plate 126 and insertion number 124. Moreover, when guide plate 126 is attached to insertion member 124, bosses 152 cooperate with lips 291 formed by attachment channels 290 to prevent relative axial displacement of guide plate 126 and insertion member 124. In this way, guide plate 126 is secured to insertion member 124 to facilitate positioning guide plate 126 atop greater trochanter 110 as described hereinabove.

After guide plate 126 is secured to greater trochanter 110, release member 134 may be actuated to position latch 138 in the position illustrated in FIG. 21 to allow for rotation of distal end 142 of insertion member 124. When latch 138 is positioned as illustrated in FIG. 21, it is no longer contained within attachment channel 290 and therefore allows relative rotation between guide plate 126 and insertion member 124. Distal end 142 of insertion member 124 is rotated to reposition bosses 152 out of axial alignment with lips 291 for removal from attachment channels 290. Insertion member 124 is thereafter removed from engagement with guide plate 126 and removed through incision 106.

Figure 3:
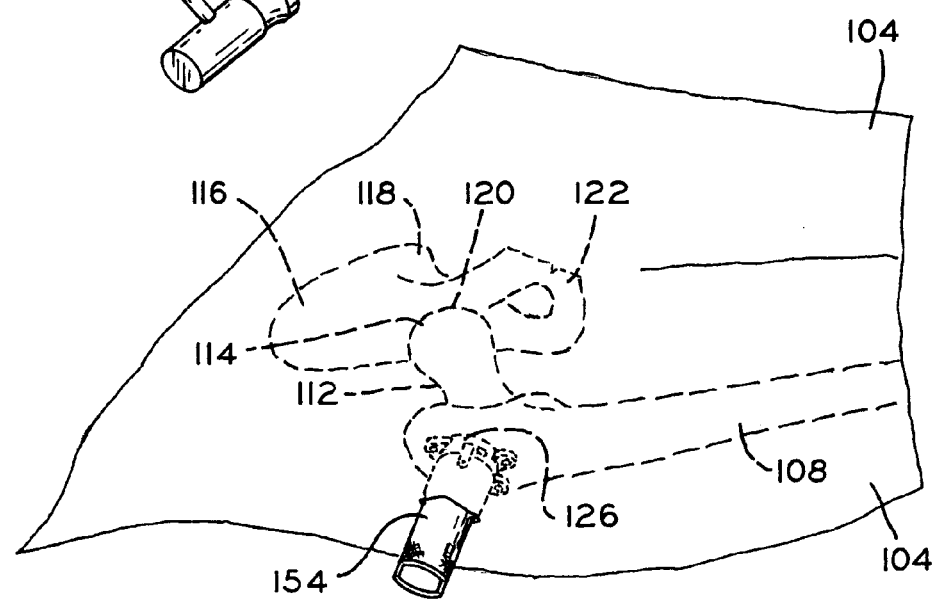
FIG. 3 is a partial perspective view illustrating a guide tube/retractor in accordance with the present invention inserted through the incision aligned with the greater trochanter and engaged with the guide plate.

After securement of guide plate 126 atop greater trochanter 110, guide tube/retractor 154 is inserted through incision 106 and releasably fixed to guide plate 126 as illustrated in FIG. 3. Guide tube/retractor 154 is illustrated in detail in FIGS. 23-27, and guide plate 126 is illustrated in detail in FIGS. 15-18. With reference to FIGS. 23-27 and 15-18, the cooperating apparatus of guide tube/retractor 154 and guide plate 126 allowing for selective locking of guide tube/retractor 154 to guide plate 126 will now be described. Fixation of guide tube/retractor 154 to guide plate 126 is effected by first positioning attachment protrusions 302 of straight guide tube/retractor 154 into attachment channels 290 of guide plate 126. Guide tube/retractor 154 is then rotated clockwise to position the radially extending portion of attachment protrusions 302 under lips 291 formed by attachment channels 290 of guide plate 126. Once rotated into this position, spring biased locking pin 294 of guide tube/retractor 154 is positioned within lock detent 292 of guide plate 126 to prevent relative rotation of guide plate 126 and guide tube/retractor 154 and lock guide tube/retractor 154 to guide plate 126.

As illustrated in FIGS. 23 and 24, spring biased locking pin 294 extends substantially axially along guide tube/retractor 154 and is operably connected to actuation member 300 to provide for manual actuation of locking pin 294. Spring 298 is operatively associated with spring biased locking pin 294 and the interior of the cylindrical wall forming guide tube/retractor 154 to bias locking pin 294 into the position illustrated in FIG. 24. When distal shoulder 303 of guide tube/retractor 154 is initially positioned atop the proximal end of guide plate 126, with attachment protrusions 302 entering attachment channels 290, locking pin 294 is moved against the biasing force of spring 298 until guide tube/retractor 154 is rotated as described hereinabove to align locking pin 294 with detent 292 and lock guide tube/retractor 154 to guide plate 126.

While the engagement of a guide tube/retractor of the present invention with guide plate 126 has been described with respect to straight guide tube/retractor 154, angled guide tube/retractor 296 is locked to guide plate 126 in the same manner utilizing the same structure as described above with respect to straight guide tube/retractor 154. The shared components of straight guide tube/retractor 154 and angled guide tube/retractor 296 are denoted with primed reference numerals. The mechanism for locking a guide tube/retractor of the present invention to guide plate 126 allows for locking of a guide tube/retractor to guide plate 126 in one of two positions separated by 180 degrees. This allows for angled guide tube/retractor 296 to provide for realignment in two directions as will be further described hereinbelow.

Guide tube/retractor 154 serves the dual purpose of maintaining an access from incision 106 to greater trochanter 110 and guiding various instruments utilized to prepare femoral cavity 224 (FIG. 11). Generally, either a straight or an angled guide tube/retractor will be utilized. FIGS. 24 and 28 respectively illustrate straight guide tube/retractor 154 and angled guide tube/retractor 296. As illustrated, e.g., in FIG. 28, angled guide tube/retractor 296 includes distal end 299 and retractor body 301. Longitudinal axis 297 of distal end 299 of angled guide tube/retractor 296 forms an angle Ø of about 10° with longitudinal axis 303 of retractor body 301. In this way, angled guide tube/retractor 296 allows for a 10° realignment with respect to straight guide tube/retractor 154. The surgeon will choose either straight guide tube/retractor 154 or angled guide tube/retractor 296 based upon the geometry of femur 108 into which implant 260 (FIG. 41) will be placed. In accordance with the present invention, an alignment device is provided to facilitate choice of straight guide tube/retractor 154 or angled guide tube/retractor 296 as well as the orientation of angled guide tube/retractor 296 as further described hereinbelow.

Figure 29:
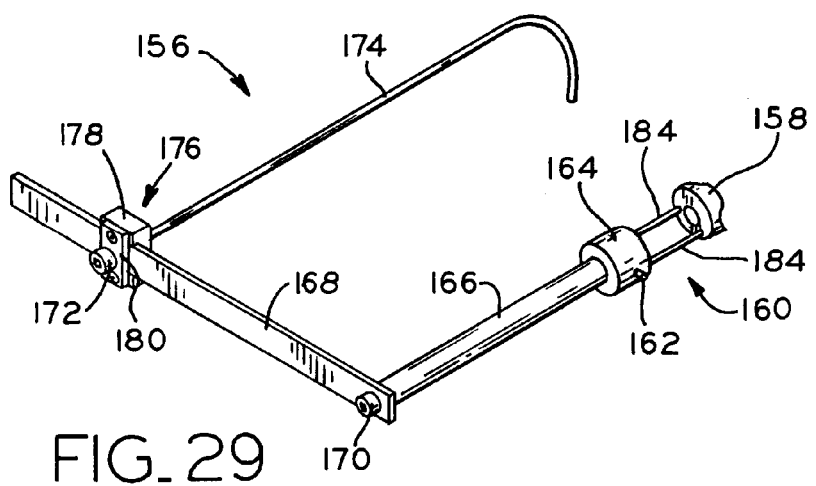
FIG. 29 is a perspective view of an alignment device of the present invention.

FIGS. 4 and 5 illustrate use of alignment device 156 to choose either straight guide tube/retractor 154 or angled guide tube/retractor 296. Alignment device 156 is illustrated in detail in FIGS. 29 and 30 and includes extension 166 connected to transverse bar 168, with alignment arm 174 slidably attached thereto. As illustrated in FIG. 29, extension 166 is connected to insertion member 160 at a distal end thereof. Insertion member 160 is sized for insertion into either straight guide tube/retractor 154 or angled guide tube/retractor 296 as illustrated in FIGS. 4 and 5.

Figure 30:
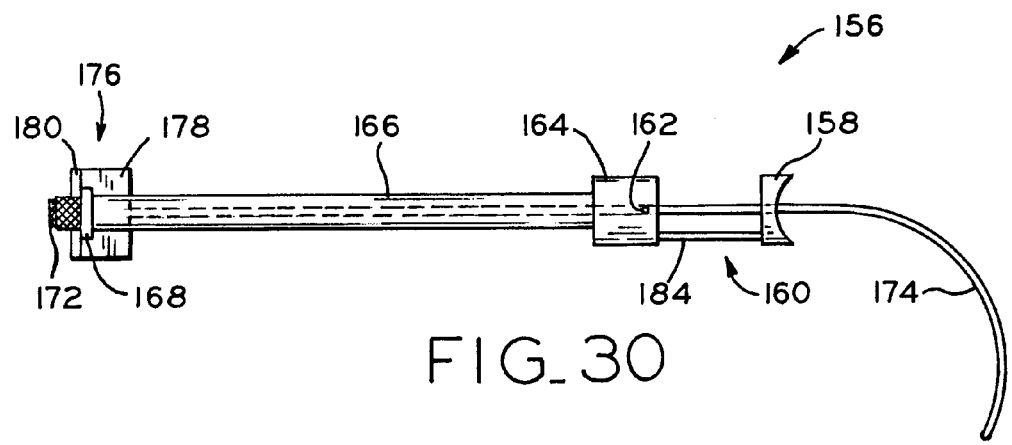
FIG. 30 is an elevational view thereof.

As illustrated in FIGS. 29 and 30, insertion portion 160 of alignment device 156 includes distal end 158 connected via connecting rods 184 to positioning cylinder 164. Positioning cylinder 164 includes a pair of opposing bosses 162, only one of which is depicted in FIGS. 29 and 30. Distal end 158 and positioning cylinder 164 have external geometries sized to cooperate with the hollow interior of the guide tube/retractors of the present invention to provide a stationary base for alignment device 156, as illustrated in FIGS. 4 and 5. Insertion portion 160 of alignment device 156 as illustrated in FIGS. 29 and 30 comprises merely one exemplary design for an insertion portion of alignment device 156 operable to stabilize alignment device 156 with the guide tube/retractors of the present invention. Generally, insertion portion 160 will include a portion thereof having an exterior geometry sized to cooperate with the interior of the guide tube/retractors of the present invention to provide a stationary base for alignment device 156. In an alternative embodiment, the insertion portion of alignment device 156 depicted in FIGS. 29 and 30 comprises a solid insertion member having a consistent cross sectional area along its length. In this embodiment, the exterior of the solid insertion member will cooperate with the interior of the guide tube/retractors of the present invention to provide a stable connection of alignment device 156 with a guide tube/retractor in accordance with the present invention.

Alignment device 156 includes transverse bar 168 fixed to extension 166 via screw 170. Positioning cylinder 164 and extension 166 provide a stable base for transverse bar 168. As illustrated in FIGS. 29 and 30, alignment arm 174 is slidably connected to transverse bar 168 via slidable attachment member 176. Slidable attachment member 176 includes attachment block 178 having a cutout therein accommodating transverse bar 168. Top plate 180 is mounted atop attachment block 178, with set screw 172 threaded therein. Set screw 172 traverses top plate 180 to selectively engage transverse bar 168 and lock alignment arm 174 in position along transverse bar 168.

As illustrated in FIGS. 4 and 5, alignment device 156 is utilized to facilitate selection of the appropriate guide tube/retractor. FIG. 5 illustrates alignment device 156 operably positioned within straight guide tube/retractor 154, which is locked to guide plate 126. In use, bosses 162 on positioning cylinder 164 are positioned within attachment channels 290 of guide plate 156 and positioning cylinder 164 is rotated until bosses 162 contact the terminal ends of channels 290 and are positioned under lips 291. After positioning alignment device 156 within guide tube/retractor 154, slidable attachment member 176 may be adjusted to accommodate the physiological characteristics of the patient and place alignment arm 174 adjacent the patient's skin. Alignment arm 174 of alignment device 156 includes a curved distal end having a curvature based on statistical data which follows a path from the central portion of greater trochanter 110, along the central axis of femoral neck 112, to the central region of femoral head 114. FIG. 5 illustrates an arrangement with the distal end of alignment arm 174 following the aforementioned path on femur 108. In the environment illustrated in FIG. 5, straight guide tube/retractor 154 is the appropriate guide tube/retractor to be utilized to effect the method of the present invention. In some cases, the distal end of alignment arm 174 will not coincide with the aforementioned path on the femur in question due to, e.g., the specific geometry of the bone in question. In this case, angled guide tube/retractor 296 may be utilized in an attempt to provide the appropriate alignment with the femur in question.

FIG. 4 illustrates alignment device 156 utilized with angled guide tube/retractor 296 on femur 108. As described above, femur 108, illustrated, e.g., in FIGS. 4 and 5 has a geometry accommodating the use of straight guide tube/retractor 154. With this in mind, FIG. 4 is useful in illustrating a situation in which the distal end of alignment arm 174 does not follow a path from the central portion of greater trochanter 110, along the central axis of femoral neck 112 to the central region of femoral head 114 and, therefore, use of the attached guide tube/retractor, i.e., angled guide tube/retractor 296 is contraindicated. Comparison of the distal end of alignment arm 174 to the aforementioned path from the central portion of the greater trochanter, along the central axis of the femoral neck to the central portion of the femoral head will be effected during surgery with the use of a fluoroscope.

Generally, straight guide tube/retractor 154 will first be locked to guide plate 126, and alignment device 156 will be operably positioned therein. A fluoroscope will then be utilized to compare the distal end of alignment arm 174 with the path from the central portion of the greater trochanter, along the central axis of the femoral neck to the central portion of the femoral head. If the distal end of alignment arm 174 does not follow the aforementioned path from the central portion of the greater trochanter to the central portion of the femoral head, then alignment device 156 and straight guide tube/retractor 154 will be removed and angled guide tube retractor 296 will be locked to guide plate 126. The angle Ø of about 10° formed between longitudinal axis 297 of distal end 299 of angled guide tube/retractor 296 and longitudinal axis 303 of retractor body 301 allows for an approximately 10 degree realignment on either side of the longitudinal axis of straight guide tube/retractor 154 in a plane substantially containing the central axis of femur 108. The inventors of the current invention have found that this 10 degree realignment in either direction typically accounts for the various bone geometries encountered. However, the inventors of the present invention further contemplate provision of additional angled guide tubes/retractors having an angle Ø as described hereinabove of other than 10 degrees. For example, Ø could measure 5°, 10°, or 15° to provide for increased versatility in performing the method of reducing a femoral fracture in accordance with the present invention.

Figure 9:
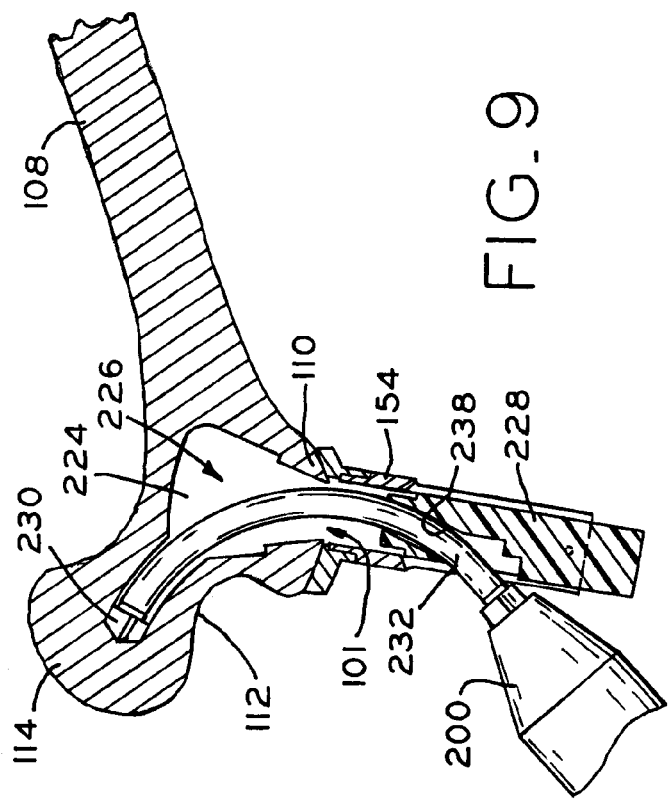
FIG. 9 is a sectional view illustrating the use of a curved femoral head reamer to extend the femoral cavity into the femoral head.
Figure 8:
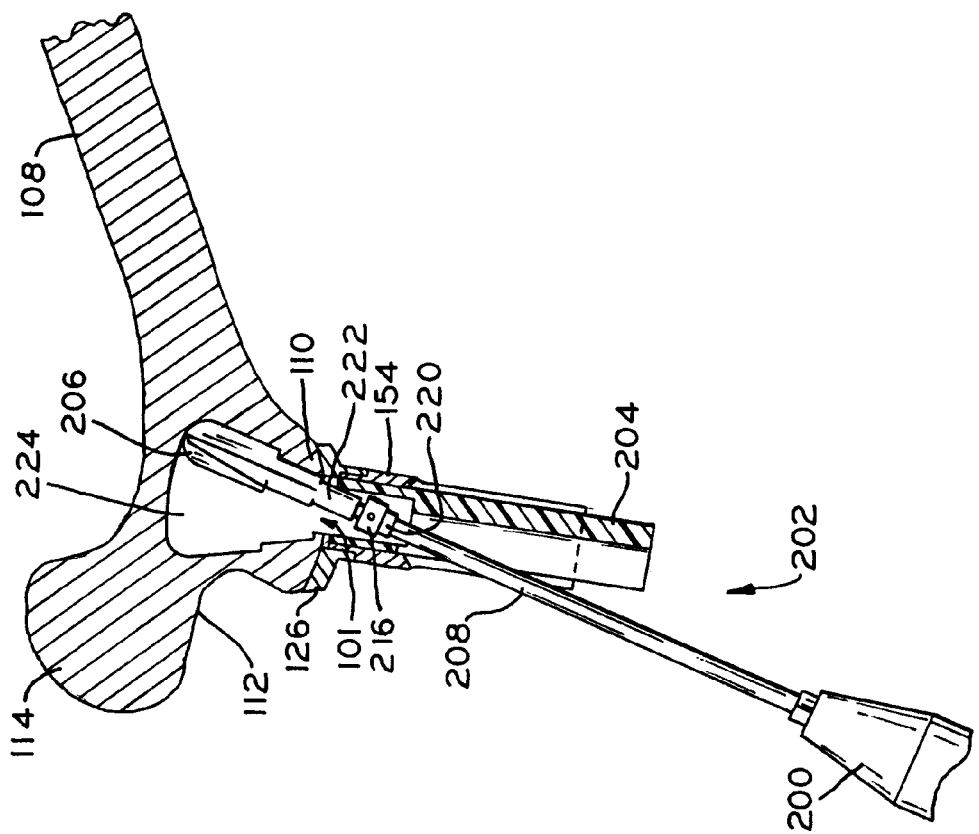
FIG. 8 is a sectional view illustrating further use of the swivel reamer depicted in FIG. 7 to form the femoral cavity.

Once the appropriate guide tube/retractor is chosen and attached to guide plate 126, cavity 224 (FIG. 11) can be formed in femur 108. As illustrated in FIG. 6, straight reamer 186 is first positioned within guide tube/retractor 154 and utilized to create access 101 in greater trochanter 110. In one exemplary embodiment, access 101 has a 1.9 centimeter (0.75 inch) diameter. After creating access 101 in greater trochanter 110, straight reamer 186 is removed from guide tube/retractor 154 and replaced with swivel reamer 202 as illustrated, e.g., in FIG. 7. As illustrated in FIG. 7, swivel reamer 202 is rotatable about pivot 216 and, in the configuration illustrated in FIG. 7, allows for the extension of femoral cavity 224 toward femoral head 114. After femoral cavity 224 is extended as illustrated in FIG. 7, swivel reamer 202 is repositioned to allow for extension of femoral cavity 224 toward the shaft of femur 108 as illustrated in FIG. 8. Swivel reamer 202 is then removed in favor of curved femoral head reamer 226. As illustrated in FIG. 9, curved femoral head reamer 226 is advanced through access 101 into femoral head 114, thus expanding femoral cavity 224 into femoral head 114. Curved femoral head reamer 226 is thereafter removed from guide tube/retractor 154 and replaced with curved femoral shaft reamer 244, as illustrated in FIG. 10. Curved femoral shaft reamer 244 is positioned through access 101 into the intramedullary canal of femur 108, as illustrated in FIG. 7, to extend femoral cavity 224 into the femoral shaft. The reaming process illustrated in FIGS. 6-10 produces femoral cavity 224 as illustrated, e.g., in FIG. 11.

Figure 31:
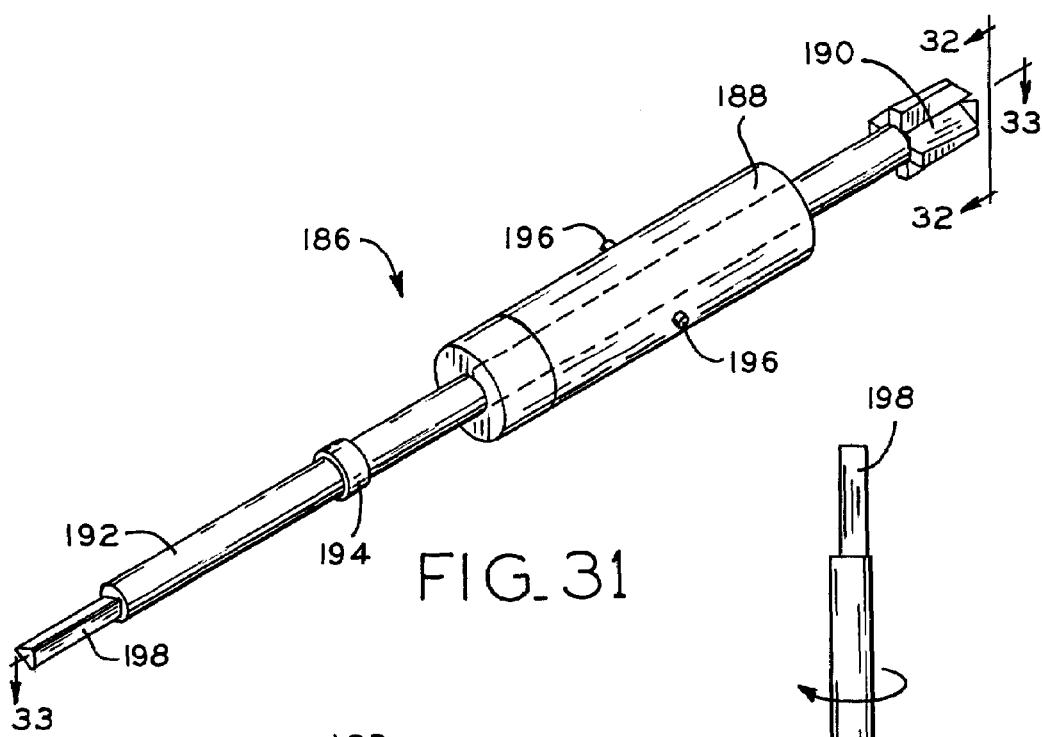
FIG. 31 is a perspective view of a plunge reamer of the present invention.
Figure 32:
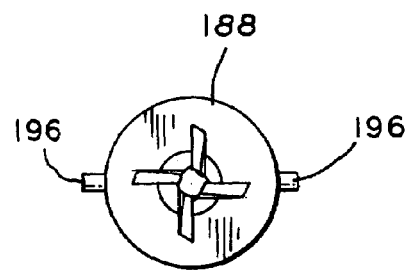
FIG. 32 is a distal axial view thereof.
Figure 33:
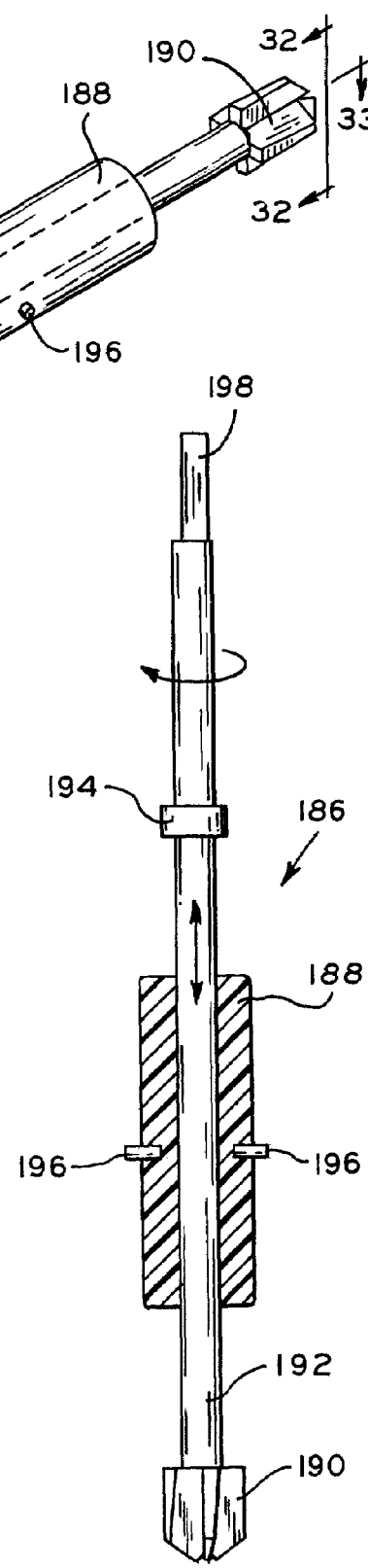
FIG. 33 is a partial sectional, elevational view thereof.

Straight reamer 186 is illustrated in detail in FIGS. 31-33. As illustrated in FIGS. 31-33, straight reamer 186 includes straight reamer guide tube 188 surrounding straight reamer shaft 192. Straight reamer guide tube 188 is positioned intermediate straight reamer head 190 and flange 194 and is operable to move along reamer shaft 192 therebetween. Straight reamer guide tube 188 as an exterior geometry cooperating with the internal geometry of straight guide tube/retractor 154 and/or angled guide tube/retractor 296 to provide a solid base for reaming femur 108 as illustrated in FIG. 6. Straight reamer 186 further includes proximal end 198 adapted to be received in chuck 200 (FIG. 6) of any of the well known rotation devices utilized to impart rotational motion to various medical instruments including, e.g., reamers. Straight reamer guide tube 188 includes opposing bosses 196 protruding from the exterior surface thereof. Bosses 196 are engagable in boss channels 304 formed in the proximal end of the guide tube/retractors of the present invention (see, e.g., FIGS. 23, 24, and 28).

In use, straight reamer guide tube 188 is positioned within a guide tube/retractor of the present invention, with bosses 196 entering boss channels 304 formed in a proximal end thereof. Guide tube 188 is then rotated until bosses 196 are positioned beneath the lip formed by the proximal end of straight guide tube/retractor of the present invention covering the radially extending portions of boss channels 304. In this position, guide tube 188 cannot readily be axially displaced with respect to the guide tube/retractor into which it is inserted. Proximal end 198 of straight reamer 186 is actuated to provide rotational movement of reamer head 190 to form access 101 in femur 108. After achieving a predetermined reamer depth, flange 194 contacts the proximal end of guide tube 188 to limit axial displacement of reamer head 190. In one exemplary embodiment, straight reamer 186 is configured to provide a reaming depth of 1.9 centimeters (0.75 inches) into femur 108.

Swivel reamer 202 is illustrated in detail in FIGS. 34-38. As illustrated in FIGS. 34-38, swivel reamer 202 includes swivel reamer guide tube 204 having opposing bosses 212 protruding therefrom. Swivel reamer guide tube 204 includes cutout 210 operable to allow reamer shaft 208 to pivot about swivel reamer pivot 216 as further described hereinbelow and as illustrated in FIG. 38. Similar to straight reamer 186, swivel reamer 202 includes proximal end 214 operable to connect swivel reamer 202 to chuck 200 (FIG. 7). Bosses 212 are utilized to connect swivel reamer 202 to a guide tube/retractor of the present invention in the same manner as bosses 196 of straight reamer 186.

As illustrated in FIG. 36, swivel reamer pivot 216 is pivotally connected to swivel reamer guide tube 204 via pivot pins 218. As illustrated in FIG. 38, swivel reamer pivot 216 is positioned about reamer shaft 218 and abuts enlarged portion 222 of swivel reamer shaft 208 and flange 220 on opposing axial ends thereof to prevent axial displacement of swivel reamer head 206. As illustrated in FIGS. 7 and 8 and described hereinabove, the orientation of swivel reamer 202 is changed 180 degrees to accommodate swivel reaming toward femoral head 114 as illustrated in FIG. 7 as well as swivel reaming toward the femoral shaft as illustrated in FIG. 8. As illustrated, e.g., in FIGS. 24 and 25, the guide tube/retractor of the present invention includes opposing cut-outs 305 to accommodate swivel reaming toward femoral head 114 as illustrated in FIG. 7 as well as swivel reaming toward the femoral shaft as illustrated in FIG. 8, without repositioning the guide tube/retractor.

Figures 39, 40:
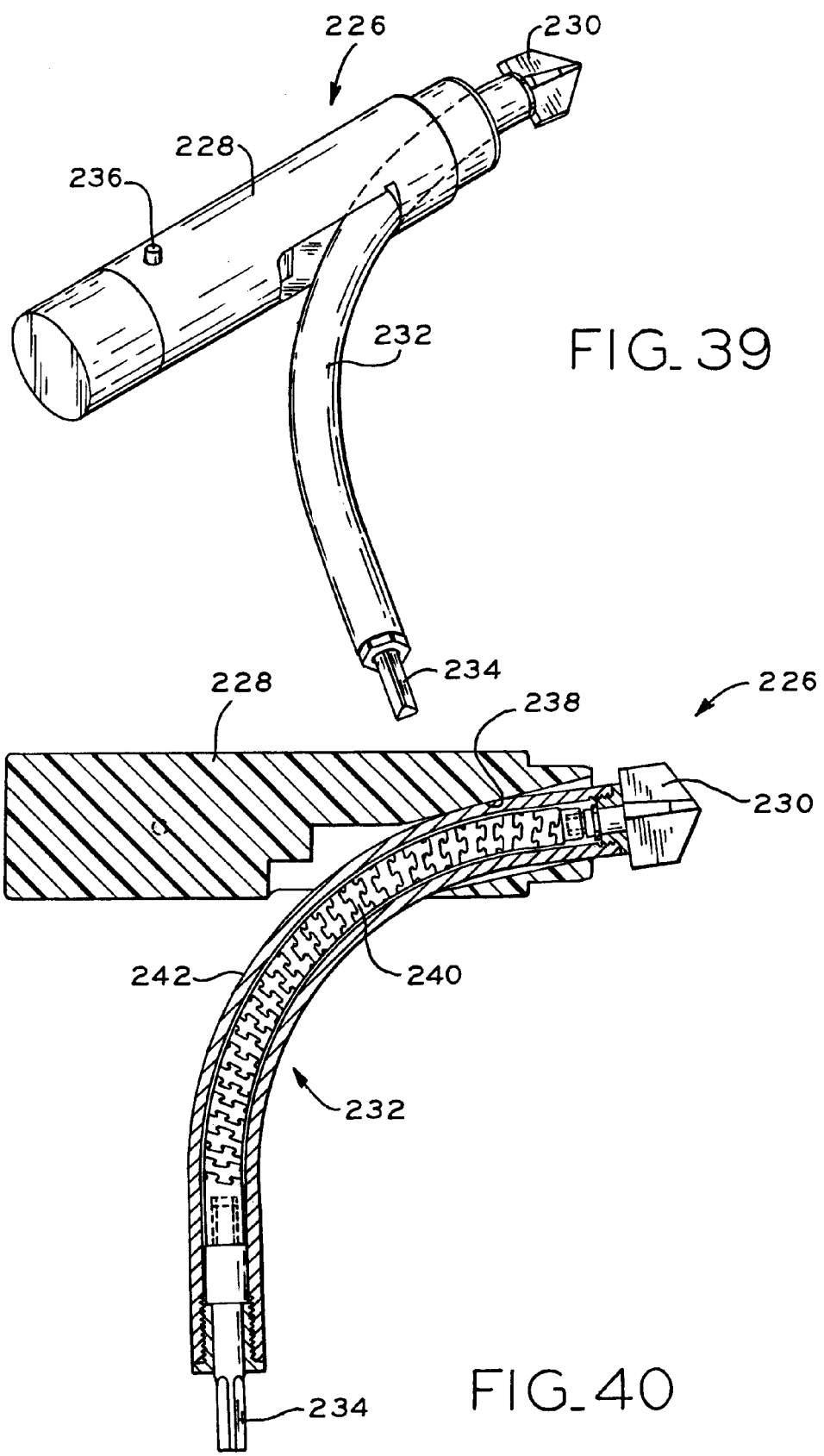
FIG. 39 is a perspective view of a curved femoral head reamer of the present invention.
FIG. 40 is a sectional view thereof.

Curved femoral head reamer 226 is illustrated in detail in FIGS. 39 and 40. As illustrated in FIGS. 39 and 40, curved femoral head reamer 226 includes guide tube 228 having bosses 236 protruding therefrom. Bosses 236 are utilized to position curved femoral head reamer 226 within guide tube/retractor of the present invention as described above with respect to straight reamer 186 and swivel reamer 202. Curved femoral head reamer 226 includes curved reamer shaft 232 having reamer head 230 operably connected to a distal end thereof. Proximal end 234 of curved reamer shaft 232 is operable to connect curved reamer 226 to chuck 200 of an actuation device as illustrated in FIG. 9. As illustrated in FIG. 40, curved reamer shaft 232 comprises a hollow shaft formed by outer tube 242. Flexible driveshaft 240 is positioned within outer tube 242 and allows for transmission of rotary motion from proximal end 234 of curved reamer 226 to reamer head 230 to effect reaming into femoral head 114 as illustrated in FIG. 9. Guide tube 228 of curved femoral head reamer 226 includes curved guide channel 238 for guiding movement of outer tube 242 of reamer shaft 232 as reamer head 230 is advanced into femoral head 114 as illustrated in FIG. 9. Curved femoral shaft reamer 242 is not illustrated in detail for the sake of brevity. Curved femoral shaft reamer 242 has an identical structure to curved femoral head reamer 226. In an exemplary embodiment of the present invention, the head of femoral shaft reamer 242 is larger than the head of curved femoral head reamer 226. Similarly, the head of curved femoral head reamer 226 may be larger than the head of curved femoral shaft reamer 242. Moreover, the radius of curvature of the reamer shafts may differ between curved femoral head reamer 226 and curved femoral shaft reamer 242. In all cases, a tubular reamer shaft and flexible driveshaft is utilized.

After formation of femoral cavity 224, any remaining guide tube/retractor as well as guide plate 126 is removed and implant 260 is positioned through access 101 to be implanted in femoral cavity 224. During implantation of implant 260, retractors are utilized to provide access from incision 106 to access 101. As illustrated in FIG. 12, bag 270 (FIG. 41) is manipulated into a relatively small package positioned about lag screw tube 266 to be positioned through access 101. In one exemplary embodiment, bag 270 is accordion folded. As further illustrated in FIG. 12, fill tube 262 and reinforcement/expansion bar 268 of femoral implant 260 are positioned adjacent lag screw tube 266 for positioning implant 260 through access 101 and into femoral cavity 224. When femoral implant 260 is fully inserted through access 101, lag screw thread 282 abuts the proximal end of femoral head arm 256 of implant cavity 224 as illustrated, e.g., in FIG. 13. In this position, fill tube 262 and reinforcement/expansion bar 268 can be manipulated into the operable position illustrated in FIG. 14. In this position, bag 270 extends into femoral shaft arm 258 of implant cavity 224. After implant 260 is positioned as illustrated in FIG. 13, a flexible drive device is utilized to advance lag screw 264 into femoral head 114 until reaching the terminal position illustrated in FIG. 14. With lag screw 264 firmly implanted in femoral head 114, pump P is utilized to convey a bag fill material for filling bag 270 from source of bag fill 284 through fill tube 262. In one exemplary embodiment, source of bag fill 284 comprises a source of bone cement. Fill tube 264 is formed to provide for retrograde filling of bag 270. As bag 270 is filled with, e.g., bone cement, it expands to fill femoral cavity 224, including, femoral shaft arm 258 thereof. Once bag 270 is filled, the bone cement injected therein cures and provides intramedullary fixation of femoral implant 260. As indicated above, in a further embodiment of the present invention, the bag structure of the implant of the present comprises a nested bag structure in which an inner bag is filled with a high strength material relative to an outer bag in which the inner bag is placed. The outer bag of this form of the present invention is formed from and filled with a more bioresorbable material relative to the material of construction and fill material of the inner bag.

Implant 260 is illustrated in detail in FIG. 41. As illustrated in FIG. 41, bag 270 is secured to lag screw tube 266 to prevent material inserted into bag 270 from escaping between the contact points formed between bag 270 and lag screw tube 266. As further illustrated in FIG. 41, reinforcement/expansion bar 268 is positioned to facilitate deployment of implant 260 into femoral shaft arm 258 of femoral cavity 224 as described hereinabove. Reinforcement/expansion bar 268 will not be utilized in every embodiment of the present invention. As illustrated in FIG. 43, reinforcement/expansion bar 268 also functions to laterally spread bag 270 to facilitate placement of bone cement therein. As illustrated in FIG. 41, fill tube 262 is positioned within bag 270, with bag 270 securely affixed to a proximal end thereof.

FIG. 90 illustrates alternative embodiment femoral implant 260'. Femoral implant 260' is generally identical to femoral implant 260 illustrated in FIG. 41 except for the provision of external fasteners 279 utilized to securely affix bag 270' to lag screw tube 266. Although not illustrated in FIG. 90, it is contemplated that femoral implant 260' will include a fill tube 262' for filling bag 270 with bone cement.

Alternative embodiments of the lag screw of the present invention are illustrated in FIGS. 42, 91, and 92. As illustrated in FIG. 42, lag screw 264 generally comprises curved lag screw shaft 274 rotatably connected to lag screw head 272. In the embodiment illustrated in FIG. 42, lag screw shaft 274 includes distal male threads 276 cooperating with proximal female threads 278 formed in lag screw head 272. Mating threads 276, 278 are left handed threads. Lag screw head 272 includes chamber 280 to accommodate distal threaded end 276 of lag screw shaft 274 when lag screw head 272 is operably positioned on lag screw shaft 274. Lag screw head 272 includes distal lag screw threads 282 for implanting lag screw 264 into femur 108 as described hereinabove. Cooperating threads 276, 278 are left handed threads, while lag screw threads 282 are right handed threads. In this way, lag screw head 272 may be threadedly engaged on lag screw shaft 274 and, rotation of lag screw head 272 in a clockwise fashion to effect implantation of lag screw threads 282 into femur 108 will not cause lag screw head 272 to become separated from lag screw shaft 274.

FIG. 91 illustrates an alternative embodiment lag screw 264' in which lag screw head 272 includes flange 277 and lag screw shaft 274 includes bearing protrusion 275. In this embodiment, bearing protrusion 275 is positioned intermediate the most proximal portion of lag screw head 272' and flange 277. In this arrangement, flange 277 cooperates with the most proximal portion of lag screw head 272 and bearing protrusion 275 to prohibit axial displacement of lag screw head 272'. Lag screw head 272' includes male hex 273' operable for connection to flexible drive 281 as illustrated in FIG. 91. In use, flexible drive 281 will be inserted within tubular lag screw shaft 274 and engaged with male hex 273' to rotate lag screw head 272 to effect implantation thereof. In the embodiment illustrated in FIG. 42, lag screw shaft 274 is similarly canulated to allow a flexible drive to enter lag screw shaft 274 and engage a cooperating protrusion (not shown) formed in lag screw head 272. FIG. 92 illustrates an alternative embodiment of lag screw head 272" wherein male threads 276" are formed on lag screw head 272", and female threads 278' are formed in lag screw shaft 274.

Alternative embodiments of guide plate 126 are illustrated in FIGS. 50-55, and 65-68. Referring now to FIGS. 50-55, guide plate 126' includes screw apertures 286' for use in securing guide plate 126 to femur 108 as described hereinabove with respect to guide plate 126. Guide plate 126' further includes spring pins 318 traversing axially oriented apertures in guide plate 126'. As illustrated in FIG. 55, spring pins 318 engage alternate ends of springs 316 to hold springs 316 in position within guide plate 126'. As illustrated in FIG. 51, guide plate 126' includes circular opening 322 as well as elliptical opening 324, with springs 316 extending into circular opening 322. In one exemplary embodiment, springs 316 are formed from titanium.

Referring now to FIGS. 65-68, guide plate 126" includes axially oriented apertures accommodating spring pins 318" in much the same way as guide plate 126' illustrated in FIGS. 50-55. Spring pins 318" are utilized to hold springs 316" in position within guide plate 126" as illustrated with respect to guide plate 126' in FIG. 55. Guide plate 126" includes circular opening 322" as well as elliptical opening 324" similar to the corresponding openings found in guide plate 126'. The distal end of guide plate 126" includes gripping teeth 404 formed therein. Additionally, guide plate 126" includes fixation screw shoulder 406 as illustrated, e.g., in FIG. 67. Fizzation screw shoulder 406 will be further described hereinbelow.

In use, guide plate 126' is inserted through incision 106 for affixation to femur 108 in the same manner as guide plate 126 described hereinabove. Insertion member 124' illustrated in FIGS. 83-86 is utilized to position guide plate 126' through incision 106 for placement atop greater trochanter 110. In many respects, insertion instrument 124' is similar to insertion instrument 124 illustrated in FIGS. 19-22 and further described hereinabove. As illustrated in FIGS. 83-86, insertion instrument 124' includes elongate aperture 132' for accommodating stabilization nail 144 (FIG. 2). Insertion member 124' includes release member 134' connected via connecting rods 348, and cylindrical connector 352 to release bars 350. Release bars 350 travel in axially oriented slots formed in the distal end of insertion member 124. The distal end of insertion member 124' includes elliptical protrusion 354 for placement within elliptical aperture 324 of guide plate 126'. Cooperation of elliptical protrusion 354 with elliptical aperture 324 insures proper rotational alignment of insertion member 124' and guide plate 126'. Upon achieving proper rotational alignment, insertion member 124' may be axially displaced into the central aperture of guide plate 126', with springs 316 engaging spring slots 326" formed in opposing sides of the distal end of insertion member 124'. In this way, springs 316 lock guide plate 126' to insertion member 124'. Bevel 317 facilitates positioning of springs 316 in spring slots 326". After guide plate 126' is secured to femur 108 as described hereinabove with respect to guide plate 126, release bars 350 are utilized to actuate springs 316 radially outwardly from their normally biased position to disengage spring slots 326" and allow for removal of insertion member 124' from guide plate 126'.

Release member 134' is utilized to effect axial displacement of release bars 350 from the position illustrated in FIG. 85 in which spring slots 326" are available for engagement with springs 316 to the position illustrated in FIG. 84 in which release bars 350 provide a radially outward force to springs 316 to allow for disengagement of insertion member 124' from locking engagement with guide plate 126' and allow for removal of insertion member 124' through incision 106. As illustrated in FIG. 85, release bars 350 include a distal bevel to facilitate movement from the position illustrated in FIG. 85 to the position illustrated in FIG. 84 to effect release of springs 316 from spring slots 326". Similarly, insertion member 124' can be lockingly engaged with guide plate 126" illustrated in FIGS. 65-68 to effect implantation of guide plate 126" through incision 106 for placement atop greater trochanter 110.

When utilizing guide plate 126" illustrated in FIGS. 65-68, plunge reamer 480 (FIG. 82) must first be utilized to form a cavity in femur 108 extending through greater trochanter 110. Plunge reamer 480 includes reamer head 484 and flange 482. In this embodiment, plunge reamer 480 is inserted through incision 106 and reamer head 484 is placed atop greater trochanter 110. As with initial placement of guide plate 126 and 126', a fluoroscope may be utilized to facilitate proper positioning of reamer head 484 atop greater trochanter 110. Furthermore, a surgeon may rely on tactile feedback for proper positioning of plunge reamer 480. Plunge reaming is effected until flange 482 abuts greater trochanter 110. Plunge reamer 480 is thereafter removed through incision 106 to allow for placement of guide plate 126" atop greater trochanter 110. Fixation screw 394 illustrated in FIGS. 61-64 is thereafter utilized to secure guide plate 126" to greater trochanter 110. While insertion instrument 124' may be utilized to initially position guide plate 126" through incision 108, it must be removed prior to implantation of fixation screw 394.

Figures 66, 67:
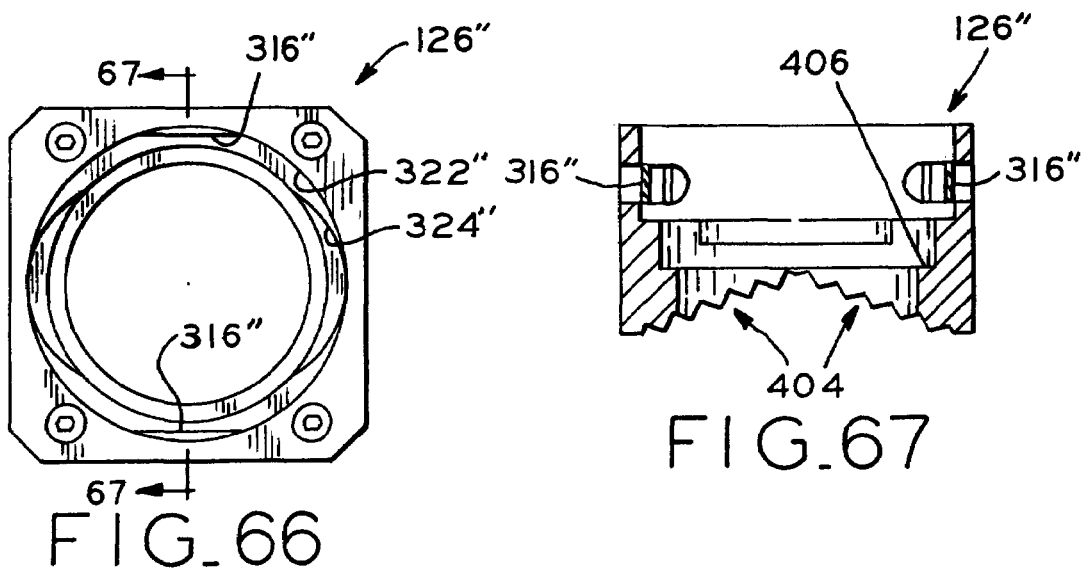
FIG. 66 is a top elevational view thereof.
FIG. 67 is a sectional view thereof taken along line 67-67 of FIG. 66.
Figure 68:
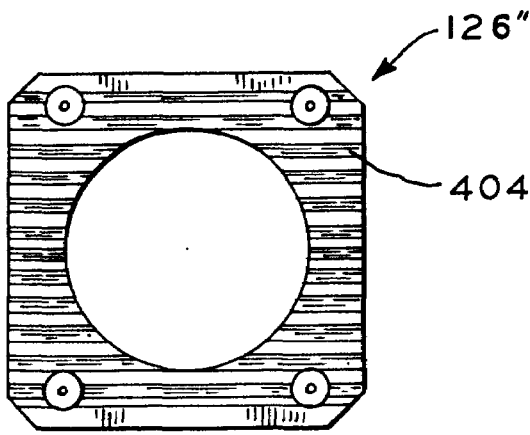
FIG. 68 is a bottom elevational view thereof.

As illustrated in FIGS. 61-64, fixation screw 394 includes fixation screw head 398 with fingers 396 axially depending therefrom. Screw threads 400 are formed on axially extending fingers 396. The proximal end of fixation screw 394 includes locking channel 402, the utility of which will be further described hereinbelow. Fixation screw head 398 forms a flange engagable with fixation screw shoulder 406 formed in guide plate 126" (FIG. 67). Fixation screw 394 is inserted through the central aperture of guide plate 126" and is screwed into the bore formed through greater trochanter 110 to secure guide plate 126" atop greater trochanter 110. Threads 400 cut into the femoral bone stock to provide fixation of fixation screw 394.

Figures 80, 81, 82:
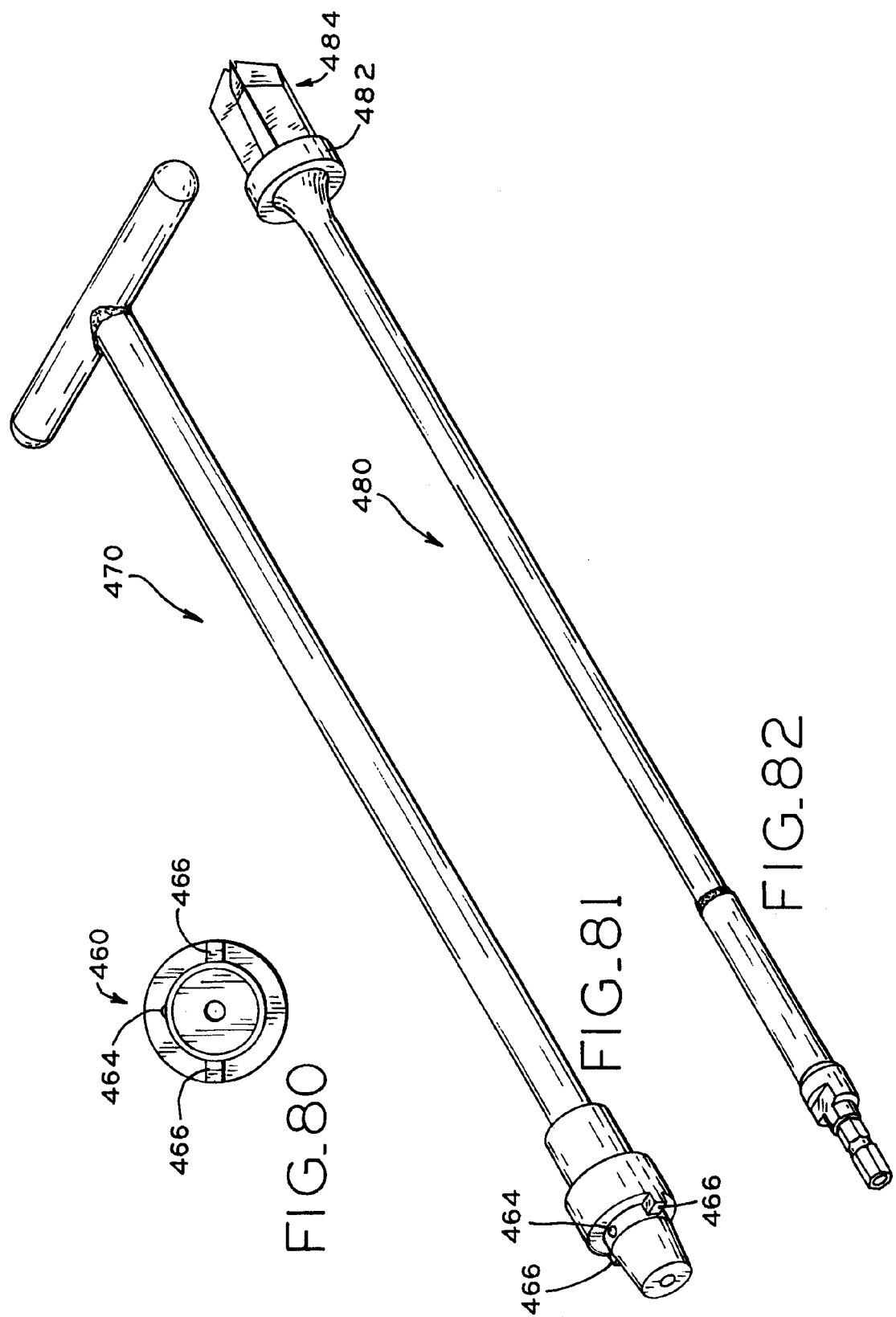
FIG. 80 is an axial view of the distal end of a fixation screw placement instrument in accordance with the present invention.
FIG. 81 is a perspective view of the fixation screw placement instrument partially illustrated in FIG. 80.
FIG. 82 is a perspective view of a straight reamer utilized to prepare the greater trochanter to receive the fixation screw illustrated in FIG. 61-64.

Fixation screw placement instrument 470 as illustrated in FIGS. 80 and 81 is utilized to insert fixation screw 394 through incision 106 and to secure fixation screw 394 within guide plate 126" as described hereinabove. Referring now to FIGS. 80 and 81, fixation screw placement instrument 470 includes a proximal handle as well as a distal end having blades 466 and ball detent 464 formed therein. In use, blades 466 engage locking channels 402 in fixation screw 394, with ball detent 464 engaging a detent (not shown) formed in the inner diameter of locking screw 394. The proximal handle of fixation screw placement instrument 470 may then be utilized to rotate fixation screw 394 and secure the same within femur 108.

When utilizing either guide plate 126' (FIGS. 50-55) or guide plate 126" (FIGS. 65-68), alternative embodiment guide tube/retractor 154' is utilized in lieu of guide tube/retractor 154 described hereinabove with reference to guide plate 126. Guide tube/retractor 154' is illustrated in FIGS. 56, 57, 59, and 60. As illustrated, guide tube/retractor 154' includes a distal end having rounded portion 330 with spring slots 326 formed on opposing sides thereof. Furthermore, distal end of guide tube/retractor 154' includes engagement protrusions 328 having a radius of curvature matching the rounded ends of elliptical openings 324 and 324" in guide plates 126' and 126", respectively. Opposing spring slots 326 formed in the distal end of guide tube/retractor 154' are utilized to selectively affix guide tube/retractor 154' to either guide plate 126' or 126" in the same fashion as described above with respect to insertion member 124'. As illustrated in FIG. 58, angled guide tube/retractor 296' is provided for use with guide plates 126' or 126". Angled guide tube/retractor 296' provides the same functionality as angled guide tube/retractor 296 described hereinabove with respect to guide plate 126 and includes a distal end identical to the distal end of straight guide tube/retractor 154 illustrated in FIGS. 56, 57, 59, and 60. Straight guide tube/retractor 154' and angled guide tube/retractor 296' have a greater axial length than straight guide tube/retractor 154 and angled guide tube/retractor 296 described in the primary embodiment of the present invention. The inventors of the present invention contemplate various guide tube/retractors having differing lengths to accommodate physiological differences in a variety of patients as well as different attaching mechanisms in accordance with the various embodiment of the present invention. As illustrated in FIGS. 56-60, guide tube/retractors 154' and 296' include latch channels 332 and 332', respectively. The utility of latch channels 332 and 332' will be further described hereinbelow.

Figure 44:
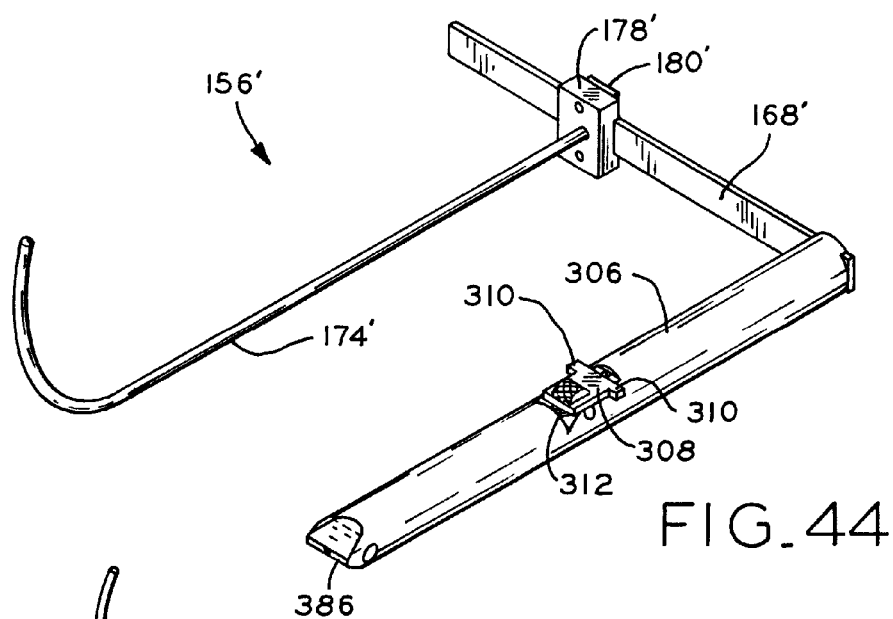
FIG. 44 is a perspective view of an alternative embodiment alignment device of the present invention.
Figure 45:
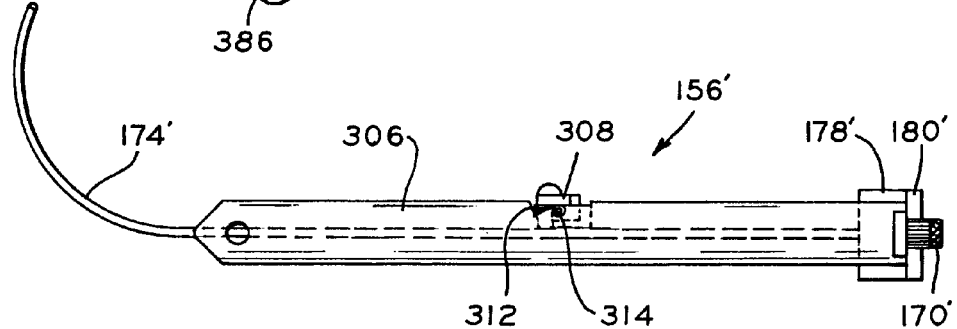
FIG. 45 is an elevational view thereof.
Figure 65:
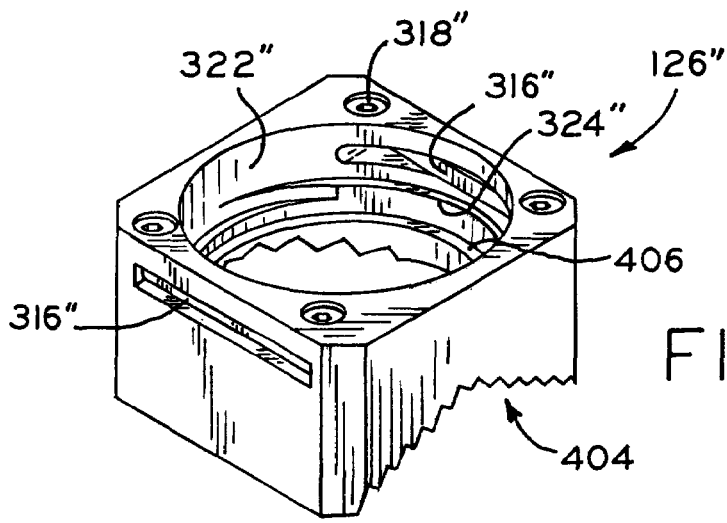
FIG. 65 is a perspective view of a second alternative embodiment guide plate in accordance with the present invention.

Referring now to FIGS. 44 and 45, alignment device 156' is utilized in conjunction with guide tube/retractors 154', 296' to select the appropriate guide tube/retractor as described hereinabove with respect to alignment device 156. Alignment device 156' includes alignment guide tube 306 for positioning within guide tube/retractor 156', or 296' and providing a stable base for alignment device 156' as described above with respect to insertion portion 160 of alignment device 156 (FIGS. 29 and 30). Alignment guide tube 306 includes latch 308 pivotally connected thereto via pivot pin 314. Additionally, alignment guide tube 306 includes distal flat 386 which, in this exemplary embodiment will bottom out on the shoulder formed between the elliptical aperture and a round aperture in guide plates 126' and 126". Latch 308 includes oppositely depending locking tabs 310 extending from opposing sides thereof. Latch 308 is biased into the position illustrated in FIG. 45 by spring 312. As alignment guide tube 306 is inserted into guide tube/retractor 156' or 296', locking tabs 310 contact the proximal end of guide tube/retractor 154' or 296'. After achieving this position, the distal end of latch 308 is depressed radially inwardly to move locking tabs 310 away from alignment guide tube 306 and allow for further insertion of alignment guide tube 306 into guide tube/retractor 154' or 296'. As indicated above, distal flat 386 bottoms out on the shoulder formed between the elliptical and the round apertures in guide plates 126' and 126" when alignment guide tube 306 is fully inserted into guide tube/retractor 154' or 296'. In this position, looking tabs 310 align with latch channels 332 and latch 308 may be allowed to return to its normally biased position as illustrated in FIG. 45. In this position, locking tabs 310 engage latch channels 332 to prevent axial displacement of alignment guide tube 306 relative to guide tube/retractor 154' or 296'. Furthermore, when engaged in latch channels 332, locking tabs 310 resist rotational movement of alignment guide tube 306. In all other respects, alignment device 156' is identical to alignment device 156 described above and is utilized in a similar fashion to choose between straight guide tube/retractor 154' and angled guide tube/retractor 296'.

Reaming of femoral cavity 224 is effected with reamers having guide tubes and latches similar to guide tube 306 and latch 308 described above with respect to alignment device 156'. In one alternative embodiment, combination reamer 358 illustrated in FIGS. 46-49 is utilized to effect both plunge, i.e., straight reaming into the femur as well as swivel reaming. In this embodiment, combination reamer 358 is inserted into guide tube/retractor 154' or 296', with orientation plate 384 cooperating with one of the longitudinal channels formed in guide tube/retractor 154' or 296' (see, e.g., FIGS. 56-60) to properly align combination reamer 358 within the guide tube/retractor. As illustrated in FIGS. 46-49, combination reamer 358 includes reamer head 360 connected to the distal end of reamer shaft 362. Reamer shaft 362 includes flange 364 positioned toward the distal end thereof and ratchet teeth 382 formed toward the proximal end thereof. As illustrated in FIG. 49, reamer shaft 362 is positioned within reamer shaft tube 372 having reamer depth lock 374 formed on a proximal end thereof. Reamer depth lock 374 includes ratchet release 376 connected via connecting rod 378 to ratchet head 380 as illustrated in FIG. 49. As illustrated in FIG. 49, a spring is utilized to bias ratchet head 380 into engagement with ratchet teeth 382 on reamer shaft 362. Ratchet release 376 is pivotally connected to reamer depth lock 374 such that actuation of ratchet release 376 causes outward radial movement of ratchet head 380 with respect to reamer shaft 362, thus disengaging the ratchet teeth formed in ratchet head 380 with ratchet teeth 382 and allowing for relative axial movement of reamer shaft tube 372 and reamer shaft 362. In the configuration illustrated in FIG. 49, combination reamer 358 can be utilized to effect plunge reaming, with the terminal reaming depth being reached when the distal end of reamer shaft tube 362 contacts pivot 216. The overall depth of plunge reaming may thus be adjusted by varying the axial displacement of reamer depth lock 374 along reamer shaft 362.

As illustrated in FIG. 46, combination reamer 358 includes combination reamer guide tube 366 having channel 368 formed therein. Swivel/plunge reaming selector 370 is operably connected to a proximal end of combination reamer guide tube 366. As illustrated in FIG. 49, rotation guide pin 388 is fixably secured to combination reamer guide tube 366 and positioned within rotation guide channel 390 of swivel/plunge reaming selector 370. Swivel/plunge reaming selector 370 may be rotated about guide tube 366 of combination reamer 358 between the extremes illustrated in FIGS. 47 and 48, i.e. with rotation guide pin 388 in opposite ends of rotation guide channel 390. When swivel/plunge reaming selector 370 is positioned as illustrated in FIG. 47, swivel reaming with combination reamer 358 is not allowed because swivel/plunge reaming selector 370 covers channel 368. To allow for swivel reaming, swivel/plunge reaming selector 370 is rotated into the position illustrated in FIG. 48. In the position illustrated in FIG. 48, channel 392 in swivel/plunge reaming selector 370 aligns with channel 368 in guide tube 366 of combination reamer 358. In this position, swivel reaming can be effected as illustrated in FIG. 48. Reamer shaft 362 is connected to guide tube 366 of combination reamer 358 via pivot 216' and pivot pins 218' to allow for the swivel reaming illustrated in FIG. 48. Combination reamer 358 includes distal flat 386' for signaling complete insertion of combination reamer 358 into reamer/guide tube 154' or 296'. As described above with respect to alignment guide tube 306 of alignment device 156', distal flat 386' bottoms out on the shoulder formed between the elliptical and round apertures in guide plates 126' and 126" when combination reamer 358 is fully inserted into guide tube/retractor 154' or 296'.

Upon completion of femoral reaming, guide tube/retractor 156' or 296' is removed from locked engagement with guide plate 126' or 126" with spring lock release instrument 336 illustrated in FIGS. 87-89. As illustrated in FIGS. 87-89, spring lock release instrument 336 includes a tubular body sized for insertion into guide tube/retractor 156' or 296' with a distal shoulder indicating complete insertion of spring lock release instrument 336 into guide tube/retractor 156' or 296' in the manner described above with respect to alignment guide tube 306 of alignment device 156', and combination reamer 358. Moreover, spring lock release instrument 336 includes latch 308' as described hereinabove with respect to guide tube 306 of alignment device 156'. After insertion of spring lock release instrument 336 into guide tube/retractor 156' or 296', handle 338 is utilized to axially displace actuation rod 342 traversing internal aperture 344 of spring lock release instrument 336 into the position illustrated in FIG. 89. In this position, the distal ramped end of actuation rod 342 contacts the proximal ends of release pins 346 to overcome the biasing force of springs 347 (FIG. 88) and cause release pins 346 to protrude from spring lock release instrument 336 as illustrated in FIG. 89. In this position, release pins 346 traverse apertures 155, 155' and act against springs 316 to disengage springs 316 from spring slots 326 and allow for removal of guide tube/retractor 154' or 296'. In the embodiment illustrated, release pins 346 are spring biased. The inventors of the current invention contemplate that release pins 346 could be linked to actuation rod 346 via a mechanical linkage whereby pulling actuation rod 342 would pull pins 346 into the instrument and, conversely, pushing rod 342 would push the pins outwardly from the instrument. Moreover, while release pins 346 are illustrated as forming an acute angle with the longitudinal axis of spring lock release instrument 336, release pins 346 could be transversely positioned within spring lock release instrument 336.

Figure 69:
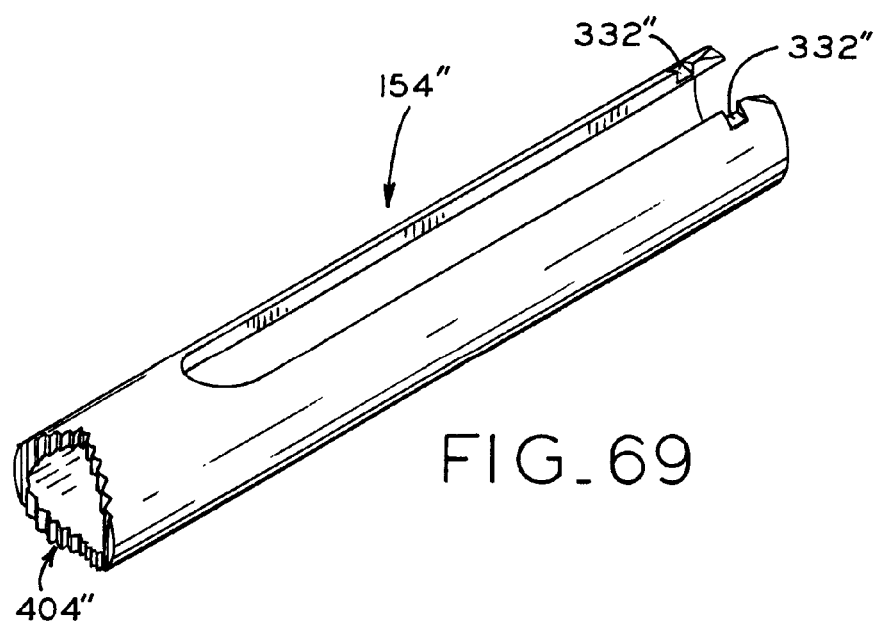
FIG. 69 is a perspective view of a second alternative embodiment guide tube/retractor in accordance with the present invention.
Figure 70:
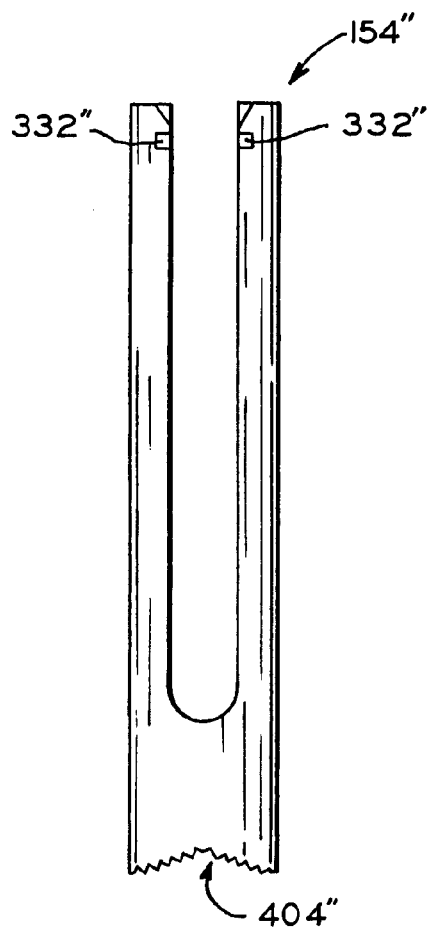
FIG. 70 is a radial elevational view thereof.

Guide tube/retractor 156" in accordance with a further alternative embodiment of the present invention is illustrated in FIGS. 69 and 70. In this embodiment, guide tube/retractor 154" is configured for affixation directly to greater trochanter 110, with guide plate 126 no longer being used. As illustrated in FIGS. 69 and 70, guide tube/retractor 154" includes gripping teeth 404" formed in a distal end thereof. Gripping teeth 404" are utilized to position guide tube/retractor 154" atop greater trochanter 110 and fixation screw 394 will be positioned within guide tube/retractor 154" and utilized to affix guide tube/retractor 154" to femur 108 as described above with reference to guide plate 126". While not illustrated in FIGS. 69 and 70, guide tube/retractor 154" includes a shoulder for engaging screw head 398 of fixation screw 394 to complete fixation of guide tube/retractor 154" to femur 108 in the same manner as described above with respect to guide plate 126".

In an alternative embodiment of the present invention, flexible reamer 428 illustrated in FIGS. 75 and 76 is utilized in lieu of the curved reamers described above to ream into femoral head 114 and into the shaft of femur 108. As illustrated in FIGS. 75 and 76, flexible reamer 428 includes reaming head 432 and flexible reaming shaft 434. As illustrated in FIG. 76, flexible reaming shaft 434 is canulated, allowing for insertion of flexible reamer shaft 434 over a guide wire to guide reaming into femoral head 114 and into the shaft of the femur 108. Flexible reamer 428 illustrated in FIGS. 75 and 76 utilizes flexible reamer guide tube 430 and a latch member associated with a particular reamer/guide tube of the present invention. However, flexible reamer 428 may include various guide tubes having physical characteristics allowing for use of flexible reamer 428 with the various guide tube/retractors of the present invention. As illustrated in FIGS. 75 and 76, the proximal end of flexible reamer shaft 434 is connected to flange 436 which acts against the proximal end of flexible reamer guide tube 430 to limit the reaming depth of flexible reamer 428.

In one exemplary embodiment, flexible reamer guide 408 (FIGS. 71 and 72) is utilized to position guide wire 410 within the femur to guide flexible reamer 428. As illustrated in FIGS. 71 and 72, flexible reamer guide 408 includes guide 416 having guide shaft fixation channel 412 formed therein. Guide 416 is insertable within guide channel 420 of the main body of flexible reamer guide 408 as illustrated in FIG. 72. Guide pegs 418 depend from guide 416 and are further inserted within guide channel 420 as illustrated in FIG. 72. Flexible reamer guide tube 486 of flexible reamer guide 408 includes advance/retract screw aperture 488 and guide wire aperture 490. With guide 416 inserted in guide channel 420 of flexible reamer guide tube 486, guide wire 410 is inserted in guide wire aperture 490 and positioned within guide shaft fixation channel 412. Set screw 414 is utilized to secure guide wire 410 within guide shaft fixation channel 412. Advance/retract screw 422 traverses a proximal aperture in guide 416 and advance/retract screw aperture 488, and is threadably engaged with receiving block 426 as illustrated in FIG. 72. Advance/retract screw 422 includes flange 424 for abutting the proximal end of guide 416 and for forcing guide 416 to be distally displaced in flexible reamer guide tube 486 in response to distal movement of advance/retract screw 422. Guide wire 410 is formed from a memory metal such as, e.g., NITINOL. With this in mind, the advance retract screw 422 may be retreated from receiving block 426 to allow guide wire 410 to retreat into guide wire aperture 490 to completely retract guide wire 410 within flexible reamer guide tube 486 of flexible reamer guide 408, without losing the ability of guide wire 410 to regain the bent shape illustrated in FIG. 71.

In use, flexible reamer guide 408 is inserted within a guide tube/retractor of the present invention with guide wire 410 not protruding from the distal end of guide wire aperture 490. The proximal end of advance retract screw 422 is thereafter actuated to force guide 416 and, consequently, guide wire 410 through flexible reamer guide tube 486 and into femoral head 414 as illustrated in FIG. 73. Once guide wire 410 achieves the position illustrated in FIG. 73, set screw 414 may be removed and flexible reamer guide 408 removed from the guide tube/retractor, leaving guide wire 410 in place within femur 108. Flexible reamer 428 may then be operably inserted in guide tube/retractor 154 as illustrated in FIG. 74 and, with guide wire 410 positioned within the canula of flexible reamer 428, femoral cavity 224 may be extended into femoral head 114 as illustrated in FIG. 74, with flexible reamer 428 being guided by guide wire 410. A similar technique may be utilized for advancing guide wire 410 into the femoral shaft to extend femoral cavity 224 therein.

Figure 77:
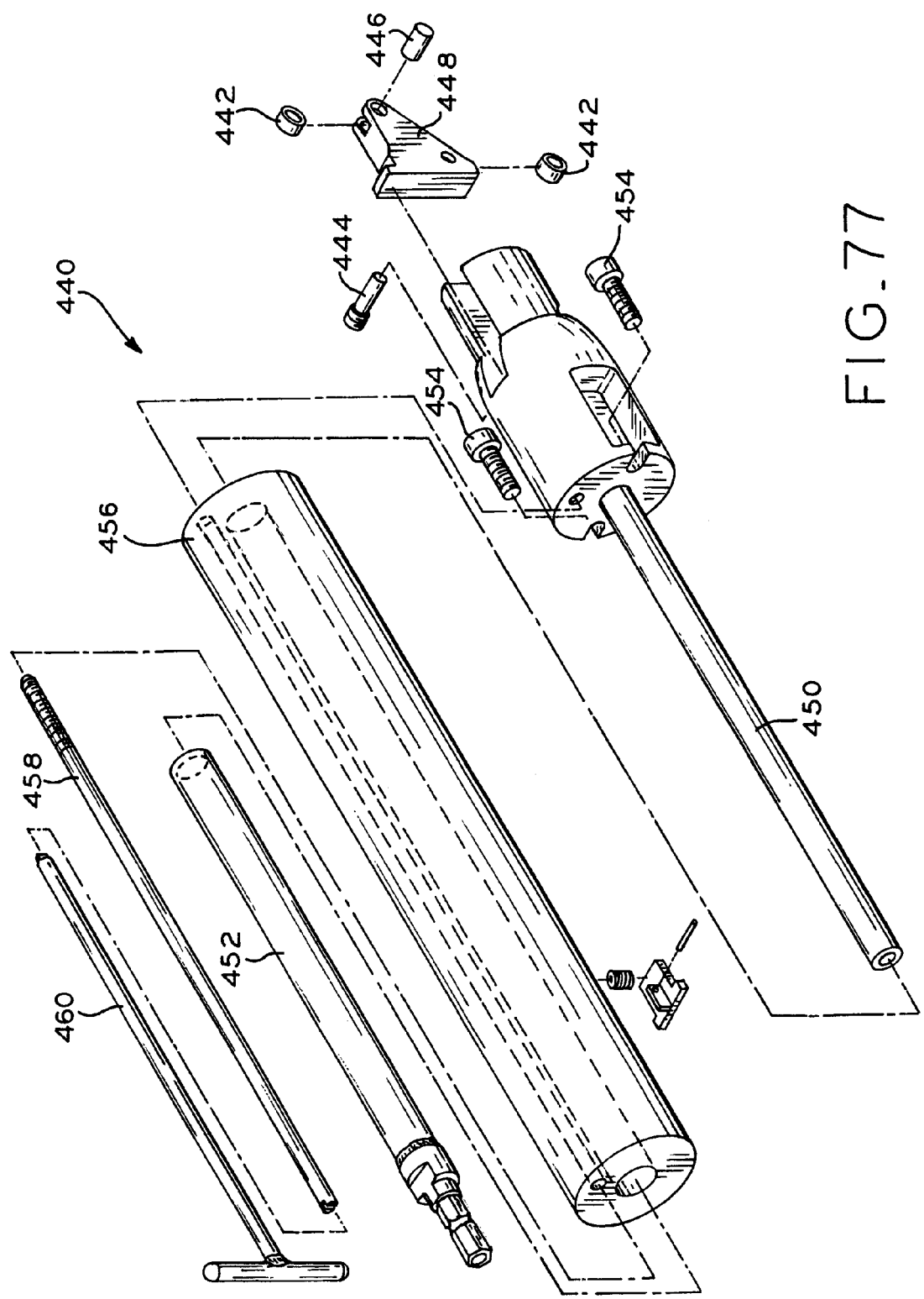
FIG. 77 is an exploded view of a flexible reamer guide wire bender in accordance with the present invention.

In a further alternative embodiment, flexible reamer guide wire bender 440 as illustrated in FIGS. 77-79 is utilized to in vivo bend a guide wire to guide reaming into, e.g., femoral head 114 as illustrated, e.g., in FIG. 73. As illustrated in FIGS. 77-79, flexible reamer guide wire bender 440 includes guide tube 456 for insertion into a guide tube/retractor of the present invention. Guide tube 456 includes a pair of elongate apertures. A first of these apertures accommodates inner wire tube 450 and outer wire tube 452 as illustrated, e.g., in FIG. 79. The second of the elongate apertures formed in guide tube 456 accommodates adjustment screw 458 as illustrated, e.g., in FIG. 79. Wire shaping head 448 is pivotally connected via pivot pin 444 to the distal end of flexible reamer guide wire bender 440 as illustrated in FIGS. 78 and 79. As illustrated in FIGS. 77 and 79, roller 442 is positioned about pivot pin 444. Wire shaping head 448 further includes roller pin 446 for connecting a second roller 442 in a rotatable manner to wire shaping head 448. As illustrated in FIG. 77, screws 454 are utilized to affix the distal end of flexible reamer guide wire bender 440 to guide tube 456. As illustrated in FIG. 79, outer wire tube 452 includes proximal wire extreme 462 against which an end of a guide wire will abut. Outer wire tube 452 is threadably engageable with either guide tube 456 or inner wire tube 450 so that outer wire tube 452 may be advanced into guide tube 456 to force a guide wire positioned against proximal wire extreme 462 through distal aperture 500 of flexible reamer guide wire bender 440. Adjustment screw 458 is utilized to rotate wire shaping head 448 about pivot pin 444 whereby rollers 442 bend a guide wire into the desired shape as it exits distal aperture 500. Shaping of a guide wire in vivo with flexible reamer guide wire bender 440 may be observed with a fluoroscope.

A guide wire bent with flexible reamer guide wire bender 440 will be advanced into, e.g., femoral head 114 as illustrated, e.g., in FIG. 73 with respect to guide wire 410. In this way, a flexible reamer will be utilized to extend femoral cavity 224 toward the femoral head as illustrated in FIG. 74. A similar procedure may be utilized for extending femoral cavity 224 into the shaft of femoral 108.

While this invention has been described as having exemplary designs, the present invention may be further modified with the spirit and scope of this disclosure. This application is therefore intended to cover any variations, uses, or adaptations of the invention utilizing its general principles. Further, this application is intended to cover such departures from the present disclosure as come within known or customary practice in the art to which this invention pertains.

What is claimed is:

1. A method of reducing a femoral fracture, comprising:
   making an incision generally aligned with a patient's greater trochanter;
   developing a wound from said incision to the greater trochanter;
   through said wound, creating a cavity in a femur, the step of creating the cavity including originating the cavity at the greater trochanter, extending the cavity from the greater trochanter into a femoral head, and extending the cavity from the greater trochanter into an intramedullary canal of the femur; and
   positioning a femoral implant in said cavity.

2. The method of claim 1, wherein said incision measures about 2-3 cm.

3. The method of claim 1, wherein said step of creating a cavity in the femur comprises:
   straight reaming into the femur through the greater trochanter to form a femoral access therethrough;
   inserting a swivel reamer into said access;
   swivel reaming to expand the cavity toward the femoral head and the femoral shaft, without enlarging said access;
   inserting a curved reamer into said access;
   advancing said curved reamer into the femoral head;
   removing said curved reamer from the femoral head; and
   advancing said curved reamer into the femoral shaft.

4. The method of claim 1, further comprising:
   affixing a guide plate to the greater trochanter;
   affixing a retractor to said guide plate, said retractor extending from the greater trochanter through said incision; and wherein said step of creating a cavity in the femur comprises creating a cavity in the femur through the retractor.

5. The method of claim 4, wherein said step of creating a cavity in the femur through the retractor comprises:
 inserting a guide wire through the greater trochanter into the femoral head;
 providing a flexible reamer having a flexible reamer guide tube, said flexible reamer guide tube having an exterior geometry, said refractor having a hollow interior, said hollow interior of said retractor and said exterior geometry of said flexible reamer guide tube cooperating to allow insertion of said flexible reamer guide tube into said retractor, whereby said flexible reamer guide tube is substantially prohibited from rotating about an axis perpendicular to a longitudinal axis thereof when said flexible reamer guide tube is inserted in said retractor;
 inserting said flexible reamer guide tube into said retractor while inserting said guide wire into a cannula of said flexible reamer;
 reaming with said flexible reamer into the femur through the greater trochanter to the femoral head with the flexible reamer, with the flexible reamer being guided by said guide wire;
 removing said guide wire and said flexible reamer from said retractor;
 inserting a guide wire through the greater trochanter into the intramedullary canal of the femur;
 inserting said flexible reamer guide tube into said retractor while inserting said guide wire into said cannula of said flexible reamer; and
 reaming from the greater trochanter into the intramedullary canal with the flexible reamer being guided by said guide wire.

6. The method of claim 5, wherein said step of inserting a guide wire through the greater trochanter into the femoral head comprises the step of inserting a guide wire shaped to follow a path from the greater trochanter to a central portion of the femoral head, and wherein said step of inserting a guide wire through the greater trochanter into the intramedullary canal of the femur comprises the step of inserting a guide wire shaped to follow a path from the greater trochanter into the intramedullary canal of the femur.

7. The method of claim 5, wherein said step of inserting a guide wire through the greater trochanter into the femoral head comprises the step of in vivo bending a guide wire to follow a path from the greater trochanter to a central portion of the femoral head while concurrently inserting said guide wire through the greater trochanter and into the femoral head, and wherein said step of inserting a guide wire trough the greater trochanter into the intramedullary canal of the femur comprises the step of in vivo bending a guide wire to follow a path from the greater trochanter to the intramedulary canal of the femur while concurrently inserting said guide wire through the greater trochanter and into the intramedulary canal.

8. The method of claim 4, wherein said step of creating a cavity in the femur through the retractor comprises:
 providing a straight reamer having a straight reamer guide tube, said straight reamer guide tube having an exterior geometry, said retractor having a hollow interior, said hollow interior of said retractor and said exterior geometry of said straight reamer guide tube cooperating to allow insertion of said straight reamer guide tube into said retractor, whereby said straight reamer guide tube is substantially prohibited from rotating about an axis perpendicular to a longitudinal axis thereof when said straight reamer guide tube is inserted in said retractor;
 inserting said straight reamer guide tube into said retractor;
 straight reaming with the straight reamer into the femur through the greater trochanter to form a femoral access therethrough;
 providing a swivel reamer having a swivel reamer guide tube and a swivel reamer head, said swivel reamer guide tube having an exterior geometry cooperating with said hollow interior of said retractor to allow insertion of said swivel reamer guide tube into said retractor, whereby said swivel reamer guide tube is substantially prohibited from rotating about an axis perpendicular to a longitudinal axis thereof when said swivel reamer guide tube is inserted in said retractor;
 inserting said swivel reamer guide tube into said retractor, and thereby inserting said swivel reamer head through said access;
 swivel reaming to expand the cavity toward the femoral head and the femoral shaft, without expanding said access;
 providing a curved reamer having a curved reamer guide tube and a curved reamer head, said curved reamer guide tube having an exterior geometry cooperating with said hollow interior of said retractor to allow insertion of said curved reamer guide tube into said retractor, whereby said curved reamer guide tube is substantially prohibited from rotating about an axis perpendicular to a longitudinal axis thereof when said curved reamer guide tube is inserted in said retractor;
 inserting said curved reamer guide tube into said retractor, and thereby inserting said curved reamer head through said access;
 advancing said curved reamer head into the femoral head;
 removing said curved reamer head from the femoral head; and
 advancing said curved reamer head into the femoral shaft.

9. The method of claim 8, wherein said straight reamer has a reamer shaft with a flange formed thereon, said flange cooperating with said straight reamer guide tube to limit a reaming depth of said straight reamer, and wherein said straight reaming step comprises straight reaming with the straight reamer into the femur through the greater trochanter until said flange contacts said proximal end of said straight reamer guide.

10. The method of claim 8, wherein said swivel reamer includes a swivel reamer head connected to a swivel reamer shaft, said swivel reamer shaft operatively connected to a pivot, whereby said swivel reamer shaft is pivotable along an axis perpendicular to a longitudinal axis of said swivel reamer shaft, and wherein said step of swivel reaming to expand the cavity toward the femoral head and the femoral shaft without expanding said access comprises the steps of:
 actuating said swivel reamer head; and
 pivoting said swivel reamer shaft about said pivot to expand the cavity toward the femoral head and femoral shaft.

11. The method of claim 8, wherein said curved reamer guide tube includes a curved guide channel, and wherein said curved reamer further includes a curved reamer shaft positioned in said curved guide channel, and wherein said step advancing said curved femoral reamer into the femoral head comprises the step of inserting said curved reamer shaft through said curved guide channel and into the femoral head, and wherein said step of advancing said curved reamer into the femoral shaft comprises advancing said curved reamer shaft through said curved guide channel into the femoral shaft.

12. The method of claim 4, further comprising:
choosing one of a straight retractor and an angled retractor prior to said step of attaching a retractor to said guide plate, and wherein said retractor attached to said guide plate comprises the retractor chosen in said choosing step.

13. The method of claim 12, wherein said step of choosing one of a straight retractor and an angled retractor comprises:
a) attaching one of said straight retractor and said angled retractor to said guide plate;
b) providing an alignment device having an extension with an exterior geometry cooperating with a hollow interior of said retractor to allow insertion of said extension into said retractor, whereby said extension is substantially prohibited from rotating about an axis perpendicular to a longitudinal axis thereof when said extension is inserted in said retractor, said alignment device further including an alignment arm having a distal end curved to follow a path from the central portion of the greater trochanter, along the central axis of the femoral neck to the central portion of the femoral head;
c) inserting said extension into said retractor;
d) comparing said alignment arm to said path on the femur; and
e) repeating steps a)-d) above until said alignment arm generally coincides with said path from the central portion of the greater trochanter, along the central axis of the femoral neck to the central portion of the femoral head.

14. The method of claim 13, wherein said comparing step comprises:
positioning said alignment arm adjacent to the patient; and
observing the path of the distal end of the alignment arm relative to a femoral path from the central portion of the greater trochanter, along the central axis of the femoral neck to the central portion of the femoral head using a fluoroscope.

15. The method of claim 12, wherein said angled retractor includes a distal end for attachment to said guide plate and a retractor body, and wherein a longitudinal axis of said distal end of said angled retractor forms an angle of about 10 degrees with a longitudinal axis of said retractor body.

16. The method of claim 4, wherein said step of affixing a guide plate to the greater trochanter comprises the steps of:
selectively attaching said guide plate to a distal end of an insertion member;
inserting said guide plate and said distal end of said insertion member into said wound;
placing said guide plate atop the greater trochanter;
using a fluoroscope, observing the placement of said guide plate atop the greater trochanter; and
repositioning said guide plate until the guide plate is positioned atop the greater trochanter.

17. The method of claim 16, wherein said step of affixing a guide plate to the greater trochanter further comprises:
inserting a stabilization nail into an elongate aperture formed in said insertion member;
impacting a proximal impact surface of said stabilization nail to drive said stabilization nail into the greater trochanter;
driving a plurality of screws through a plurality of screw apertures formed in said guide plate and into the greater trochanter, whereby said screws retain the position of said guide plate atop the greater trochanter; and
removing said stabilization nail from engagement with the greater trochanter; and
removing said insertion member from said guide plate.

18. The method of claim 4, wherein said step of creating a cavity in the femur through the retractor comprises:
providing a combination reamer having a combination reamer guide tube and a combination reamer head, said combination reamer guide tube having an exterior geometry, said retractor having a hollow interior, said hollow interior of said retractor and said exterior geometry of said combination reamer guide tube cooperating to allow insertion of said combination reamer guide tube into said retractor, whereby said combination reamer guide tube is substantially prohibited from rotating about an axis perpendicular to a longitudinal axis thereof when said combination reamer guide tube is inserted in said retractor;
inserting said combination reamer guide tube into said retractor;
straight reaming with the combination reamer into the femur through the greater trochanter to form a femoral access therethrough;
adjusting said combination reamer to accommodate swivel reaming;
swivel reaming to expand the cavity toward the femoral head and the femoral shaft, without expanding said access;
providing a curved reamer having a curved reamer guide tube and a curved reamer head, said curved reamer guide tube having an exterior geometry cooperating with said hollow interior of said retractor to allow insertion of said curved reamer guide tube into said retractor, whereby said curved reamer guide tube is substantially prohibited from rotating about an axis perpendicular to a longitudinal axis thereof when said curved reamer guide tube is inserted into said retractor;
inserting said curved reamer guide tube into said retractor, and thereby inserting said curved reamer head through said access;
advancing said curved reamer head into the femoral head;
removing said curved reamer head from the femoral head;
removing said curved reamer guide tube from said retractor;
reinserting said curved reamer guide tube into said retractor, and thereby inserting said curved reamer head through said access; and
advancing said curved reamer head into the intramedullary canal.

19. The method of claim 1, wherein said step of creating a cavity in the femur comprises:
positioning a plunge reamer through the incision and atop the greater trochanter; actuating the plunge reamer;
reaming with the plunge reamer through the greater trochanter into the femur to form a portion of said cavity in the femur;
removing the plunge reamer through the incision;
inserting a guide plate through said incision;
placing said guide plate atop the greater trochanter, a central aperture of said guide plate aligned with said portion of said cavity;
securing said guide plate to the greater trochanter utilizing a cannulated fixation screw allowing access to said portion of said cavity; and
creating said cavity in the femur through said guide plate.

20. The method of claim 19, wherein said step of securing said guide plate to the greater trochanter comprises the steps of:
   inserting said cannulated fixation screw through said incision, through said central aperture, and into said portion of said cavity; and
   threading said fixation screw into said portion of said cavity until a head of said fixation screw abuts a shoulder of said guide plate and said guide plate is secured intermediate the femur and said fixation screw.

21. The method of claim 19, wherein said step of creating said cavity in the femur through said guide plate further comprises the steps of:
   affixing a retractor to said guide plate, said retractor extending from the greater trochanter through said incision; and
   creating said cavity in the femur through both said guide plate and said retractor.

22. The method of claim 1, wherein said step of creating a cavity in the femur comprises:
   positioning a plunge reamer through the incision and atop the greater trochanter; actuating the plunge reamer;
   reaming with the plunge reamer through the greater trochanter into the femur to form a portion of said cavity in the femur;
   removing the plunge reamer through the incision;
   inserting a retractor through said incision;
   placing said retractor atop the greater trochanter, a central aperture of said retractor aligned with said portion of said cavity, said retractor extending from the greater trochanter through said incision;
   securing said retractor to the greater trochanter utilizing a cannulated fixation screw allowing access to said portion of said cavity; and
   creating said cavity in the femur through said refractor.

23. The method of claim 22, wherein said step of securing said retractor to the greater trochanter comprises the steps of:
   inserting said cannulated fixation screw through said incision, through said central aperture, and into said portion of said cavity; and
   threading said fixation screw into said portion of said cavity until a head of said fixation screw abuts a shoulder of said retractor and said retractor is secured intermediate the femur and said fixation screw.

24. The method of claim 1, wherein said cavity extends from a lateral side of the greater trochanter into the femoral head and from the lateral side of the greater trochanter into the intramedullary canal of the femur.

25. The method of claim 1, wherein said cavity originates from a single access portal formed in the greater trochanter.

26. A method of reducing a femoral fracture, comprising:
   making an incision generally aligned with a patient's greater trochanter;
   developing a wound from said incision to the greater trochanter;
   through said wound, creating a cavity in a femur, said cavity extending from the greater trochanter into a femoral head, said cavity further extending from the greater trochanter into an intramedullary canal of the femur; and
   positioning a femoral implant in said cavity, wherein said step of positioning a femoral implant in said cavity comprises:
      inserting said femoral implant into an access formed in the greater trochanter, said access intersecting said cavity, said femoral implant comprising:
         a bag;
         a lag screw tube; and
         a lag screw;
      advancing said lag screw through said lag screw tube and into the femoral head; and
      filling said bag with a substance to expand said bag to substantially fill said cavity.

27. The method of claim 26, wherein said substance comprises bone cement.

28. The method of claim 26, wherein said bag comprises an acrylic bag.

29. The method of claim 26, wherein said cavity extends from a lateral side of the greater trochanter into the femoral head and from the lateral side of the greater trochanter into the intramedullary canal of the femur.

* * * * *